(12) United States Patent
Lanci et al.

(10) Patent No.: US 10,676,413 B2
(45) Date of Patent: *Jun. 9, 2020

(54) PRODUCTION AND SEPARATION OF DIMETHYL BIPHENYL ISOMERS

(71) Applicant: ExxonMobil Research and Engineering Company, Annandale, NJ (US)

(72) Inventors: Michael P. Lanci, Flemington, NJ (US); Changyub Paek, Bridgewater, NJ (US); Catherine M. Dorsi, Houston, TX (US)

(73) Assignee: ExxonMobil Research & Engineering Company, Annandale, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/365,976

(22) Filed: Mar. 27, 2019

(65) Prior Publication Data

US 2019/0300457 A1 Oct. 3, 2019

Related U.S. Application Data

(60) Provisional application No. 62/650,495, filed on Mar. 30, 2018.

(51) Int. Cl.
*C07C 7/12* (2006.01)
*C07C 7/13* (2006.01)
(Continued)

(52) U.S. Cl.
CPC .............. *C07C 15/14* (2013.01); *C07C 7/04* (2013.01); *C07C 7/10* (2013.01)

(58) Field of Classification Search
CPC .................................. C07C 7/12; C07C 7/13
(Continued)

(56) References Cited

U.S. PATENT DOCUMENTS

| 3,626,020 A | 12/1971 | Neuzil |
| 3,699,182 A | 10/1972 | Cattanach |

(Continued)

FOREIGN PATENT DOCUMENTS

| WO | 2014117076 A1 | 7/2014 |
| WO | 2014117076 A9 | 7/2015 |

(Continued)

OTHER PUBLICATIONS

Baertsch et al., "Permeation of aromatic hydrocarbon vapors through silicalite-zeolite membranes", J. Phys. Chem, 1996, vol. 100, pp. 7676-7679.

(Continued)

*Primary Examiner* — Thuan D Dang
(74) *Attorney, Agent, or Firm* — Priya G. Prasad

(57) ABSTRACT

In a process for producing one or more 2,X'-dimethyl biphenyl isomers (where X=2, 3 or 4), a feed comprising toluene is contacted with hydrogen in the presence of a hydroalkylation catalyst under conditions effective to produce a hydroalkylation reaction product comprising (methylcyclohexyl)toluene. At least part of the hydroalkylation reaction product is dehydrogenated in the presence of a dehydrogenation catalyst under conditions effective to produce a dehydrogenation reaction product comprising dimethyl biphenyl isomers. The dehydrogenation reaction product is then separated into at least a first stream comprising one or more 3,3'-, 3,4'- and 4,4'-dimethyl biphenyl isomers and at least one second stream comprising one or more 2,X'-dimethyl biphenyl isomers (where X=2, 3 or 4). The at least one second stream is then contacted with a first adsorbent thereby selectively adsorbing one or more 2,X'-dimethyl biphenyl isomers (where X=2, 3 or 4) within said first adsorbent and then withdrawing from said first adsorbent a first extract stream comprising one or more selec- (Continued)

tively adsorbed 2,X'-dimethyl biphenyl isomers (where X=2, 3 or 4) and a first raffinate stream comprising one or more less selectively adsorbed components.

10 Claims, 13 Drawing Sheets

(51) Int. Cl.
 C07C 15/14 (2006.01)
 C07C 7/10 (2006.01)
 C07C 7/04 (2006.01)
(58) Field of Classification Search
 USPC .................................. 585/827, 826, 828
 See application file for complete search history.

(56) References Cited

U.S. PATENT DOCUMENTS

| | | | |
|---|---|---|---|
| 4,127,598 A * | 11/1978 | McEntee | C07F 7/20 556/442 |
| 6,730,625 B1 | 5/2004 | Chang et al. | |
| 8,580,120 B2 | 8/2013 | Porter | |
| 9,085,669 B2 | 7/2015 | Dakka et al. | |
| 9,328,053 B2 | 5/2016 | Bai et al. | |
| 9,580,572 B2 | 2/2017 | Dakka et al. | |
| 9,663,417 B2 | 5/2017 | Dakka et al. | |
| 9,688,602 B2 | 6/2017 | Dakka et al. | |
| 9,896,393 B2 | 2/2018 | Salciccioli et al. | |
| 2009/0326310 A1 | 12/2009 | Kulprathipanja et al. | |
| 2016/0176785 A1 | 6/2016 | Salciccioli et al. | |

FOREIGN PATENT DOCUMENTS

| | | |
|---|---|---|
| WO | 2015112252 A1 | 7/2015 |
| WO | 20150191289 A1 | 12/2015 |

OTHER PUBLICATIONS

Foster et al., "A geometric solution to the largest-free-sphere problem in zeolite frameworks", Micropo. Mesopor. Mat., 2006, vol. 90, pp. 32-38.
Funke et al., "Separation of close-boiling hydrocarbons with silicalite zeolite", J. Chem. Soc. Faraday Trans., 1996, vol. 92, pp. 2499-2502.
Minceva et al., "Modeling and simulation of a simulated moving bed for the separation of p-xylene", Ind. Eng. Chem. Res., 2002, vol. 41, pp. 3454-3461.
Minceva et al., "Understanding and revamping of industrial scale SMB units for p-xylene separation", AIChE Journal, 2007, vol. 53, pp. 138-149.
Pais et al., "Chiral separation by SMB chromatography", Sep. Pur. Tech., 2000, vol. 20, pp. 67-77.
Rajendran et al., "Simulated moving bed chromatography for the separation of enantiomers", J. Chrom. A, 2009, vol. 1216, pp. 709-738.
Silva et al., "Fixed-bed adsorption of aromatic C8 isomers: Breakthrough experiments, modeling and simulation", 2012, vol. 90, pp. 246-256.
Silva et al., "Modeling and simulation of an industrial-scale parex process", AIChE Journal, 2015, vol. 61, pp. 1345-1363.
Tokay et al., "Nanopaiticle silicalite-1 crystallization from clear solutions: Nucleation", Micropor. Mesopor. Mat., 2009, vol. 118, pp. 143-151.
Ruthven et al., "Counter-Current and Simulated Counter-Current Adsorption Separation Processes", Chem. Eng. Sci., 1989, vol. 44, pp. 1011-1038.

* cited by examiner

PRODUCTION AND SEPARATION OF DIMETHYL BIPHENYL ISOMERS

CROSS-REFERENCE TO RELATED APPLICATIONS

This application claims priority to U.S. Provisional Application Ser. No. 62/650,495 filed Mar. 30, 2018, which is herein incorporated by reference in its entirety.

FIELD

This disclosure relates to the production and separation of dimethyl biphenyl isomers, wherein separation is facilitated by selective adsorption.

BACKGROUND

Dimethyl biphenyl (DMBP) compounds are useful intermediates in the production of a variety of commercially valuable products, including polyesters and plasticizers for PVC and other polymer compositions. DMBP compounds can be readily converted to an ester plasticizer by a process comprising oxidation of the DMBP to produce the corresponding mono- or dicarboxylic acid followed by esterification with a long chain alcohol.

For example, 4,4'-biphenyl-dicarboxylic acid, optionally together with 3,4'-biphenyl dicarboxylic acid, is a potential precursor, either alone or as a modifier for polyethylene terephthalate (PET), in the production of polyester fibers, engineering plastics, liquid crystal polymers for electronic and mechanical devices, and films with high heat resistance and strength.

Processes to produce DMBP compounds generally yield a mixture of all six DMBP isomers, namely 2,2'-, 2,3'-, 2,4'-, 3,3'-, 3,4'- and 4,4'-DMBP (see, for example, International Patent Application Publication No. WO 2015/112252).

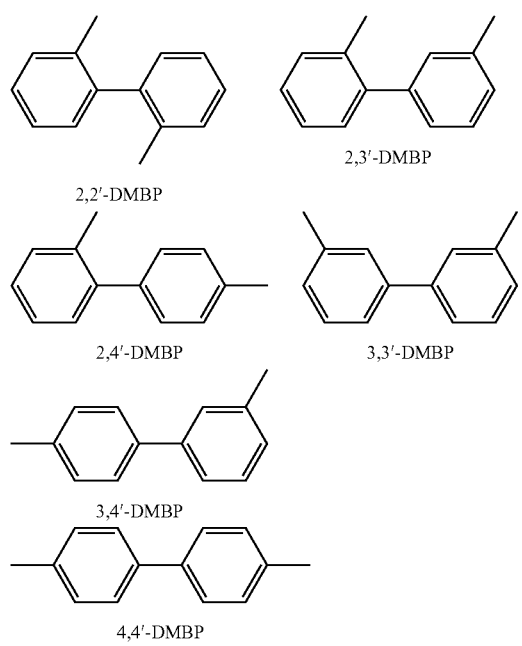

Such processes also yield DMBP containing product streams comprising other non-DMBP components, including one or more of cyclopentadienyl toluenes (CPDTs), 4-methylcyclohexyl toluenes (4,X'-MCHTs, where X=2, 3 or 4), 3-methylcyclohexyl toluenes (3,X'-MCHTs, where X=2, 3 or 4), 2-methylcyclohexyl toluenes (2,X'-MCHTSs, where X=2, 3 or 4), 1-methylcyclohexyl toluenes (1,X'-MCHTs, where X=2, 3 or 4), ethyl- or dimethyl-cyclopentyl toluenes (CPTs), and dimethyl bicyclohexanes (DMBCHs).

For certain applications, it is desirable to maximize the purity of individual DMBP isomers, particularly the 3,3'-, 3,4'- and 4,4'-DMBP isomers. However, in view of the proximity of the boiling points of the components in the DMBP product stream, separation based on distillation is challenging (see Table 1 below).

TABLE 1

| Isomer | Normal Boiling Point (° C.) | Fusion Temperature (° C.) |
|---|---|---|
| 1,X'-MCHT | 270 | |
| 2,2'-MCHT | 269 | |
| 2,3'-MCHT | 269 | |
| 2,4'-MCHT | 275 | |
| 3,2'-MCHT | 271 | |
| 3,3'-MCHT | 270 | |
| 3,4'-MCHT | 271 | |
| 4,2'-MCHT | 272 | |
| 4,3'-MCHT | 271 | |
| 4,4'-MCHT | 273 | |
| 2,2'-DMBP | 261 | 19 |
| 2,3'-DMBP | 272 | |
| 2,4'-DMBP | 275 | −24 |
| 3,3'-DMBP | 289 | 8 |
| 3,4'-DMBP | 293 | 12 |
| 4,4'-DMBP | 296 | 115 |

Based on boiling point differences it is possible to separate the DMBP product stream into a first stream comprising the 3,3'-, 3,4'- and 4,4'-DMBP isomers and a second stream comprising a mixture of the 2,X'-DMBP isomers, where X=2, 3 or 4, and the various MCHT isomers, utilizing, for example, fractional distillation.

However, it would also be desirable to separate the 2,X'-DMBP isomers (where X=2, 3 or 4) from the MCHT components so that the 2,X'-DMBP isomers may be converted into the more desirable 3,3'-, 3,4'- and 4,4'-DMBP isomers. However, in view of the very close boiling points of the 2,X'-DMBP isomers to those of the MCHT components this is challenging.

Furthermore, separation of the 3,3'-, 3,4'- and 4,4'-DMBP isomers from each other based on boiling point also presents a challenge, particularly separation of the 3,4'-isomer from the 4,4'-isomer which have very close boiling points. Based on heat of fusion differences it is in principle possible to effect separation of 3,3'-, 3,4'- and 4,4'-DMBP isomers via crystallization. However, because the relative proportions of some of these isomers in a mixture may be small, separation by crystallization may not be commercially attractive.

In view of the above, it would be desirable to provide alternative processes for the production and separation of DMBP isomers, particularly processes that may improve the overall yield of the desirable 3,3'-, 3,4'- and 4,4'-DMBP isomers and provide each of these isomers in an isomerically pure form.

It is known that certain adsorbents, for example zeolites, can be used to separate individual hydrocarbons from mixtures thereof. Adsorptive separation may be useful where the components to be separated have similar physical properties such as boiling point and melting points. For example, utilizing zeolites it is possible to selectively separate a predetermined xylene from a mixture of xylene isomers.

See, for example, United States Patent Application Publication No. 2009/0326310 and references therein.

The reference in this specification to any prior publication (or information derived from it), or to any matter which is known, is not, and should not be taken as an acknowledgement or admission or any form of suggestion that the prior publication (or information derived from it) or known matter forms part of the common general knowledge in the field of endeavour to which this specification relates.

SUMMARY

In a first aspect of the present disclosure there is provided a process for separating one or more 2,X'-dimethyl biphenyl isomers (where X=2, 3 or 4) from a mixture comprising the same, the process comprising:

(a) contacting the mixture with a first adsorbent thereby selectively adsorbing one or more 2,X'-dimethyl biphenyl isomers (where X=2, 3 or 4) within said first adsorbent;

(b) withdrawing from said first adsorbent a first raffinate stream comprising one or more less selectively adsorbed components; and (c) withdrawing from said first adsorbent a first extract stream comprising said one or more selectively adsorbed 2,X'-dimethyl biphenyl isomers (where X=2, 3 or 4).

In a second aspect of the present disclosure there is provided a process for producing one or more 2,X'-dimethyl biphenyl isomers (where X=2, 3 or 4), the process comprising:

(a) contacting a feed comprising toluene with hydrogen in the presence of a hydroalkylation catalyst under conditions effective to produce a hydroalkylation reaction product comprising (methylcyclohexyl)toluenes;

(b) dehydrogenating at least part of the hydroalkylation reaction product in the presence of a dehydrogenation catalyst under conditions effective to produce a dehydrogenation reaction product comprising said dimethyl biphenyl isomers;

(c) separating the dehydrogenation reaction product into at least a first stream comprising one or more 3,3'-, 3,4'- and 4,4'-dimethyl biphenyl isomers and at least one second stream comprising one or more 2,X'-dimethyl biphenyl isomers (where X=2, 3 or 4);

(d) contacting the at least one second stream with a first adsorbent thereby selectively adsorbing one or more 2,X'-dimethyl biphenyl isomers (where X=2, 3 or 4) within said first adsorbent;

(e) withdrawing from said first adsorbent a first raffinate stream comprising one or more less selectively adsorbed components; and (f) withdrawing from said first adsorbent a first extract stream comprising one or more
selectively adsorbed 2,X'-dimethyl biphenyl isomers (where X=2, 3 or 4).

In a third aspect of the present disclosure there is provided a process for producing one or more 3,3'-, 3,4'- and 4,4'-dimethyl biphenyl isomers, the process comprising:

(a) contacting a feed comprising toluene with hydrogen in the presence of a hydroalkylation catalyst under conditions effective to produce a hydroalkylation reaction product comprising (methylcyclohexyl)toluenes;

(b) dehydrogenating at least part of the hydroalkylation reaction product in the presence of a dehydrogenation catalyst under conditions effective to produce a dehydrogenation reaction product comprising said dimethyl biphenyl isomers;

(c) separating the dehydrogenation reaction product into at least a first stream comprising one or more 3,3'-, 3,4'- and 4,4'-dimethyl biphenyl isomers and at least one second stream comprising one or more 2,X'-dimethyl biphenyl isomers (where X=2, 3 or 4);

(d) contacting the at least one second stream with a first adsorbent thereby selectively adsorbing one or more 2,X'-dimethyl biphenyl isomers (where X=2, 3 or 4) within the first adsorbent;

(e) withdrawing from said first adsorbent a first raffinate stream comprising one or more less selectively adsorbed components;

(f) withdrawing from said first adsorbent a first extract stream comprising one or more selectively adsorbed 2,X'-dimethyl biphenyl isomers (where X=2, 3 or 4);

(g) contacting said first extract stream with an isomerization catalyst under conditions effective to produce an isomerization effluent comprising one or more 3,3'-, 3,4'- or 4,4'-dimethyl biphenyl isomers.

DETAILED DESCRIPTION OF THE EMBODIMENTS

Figure 1:
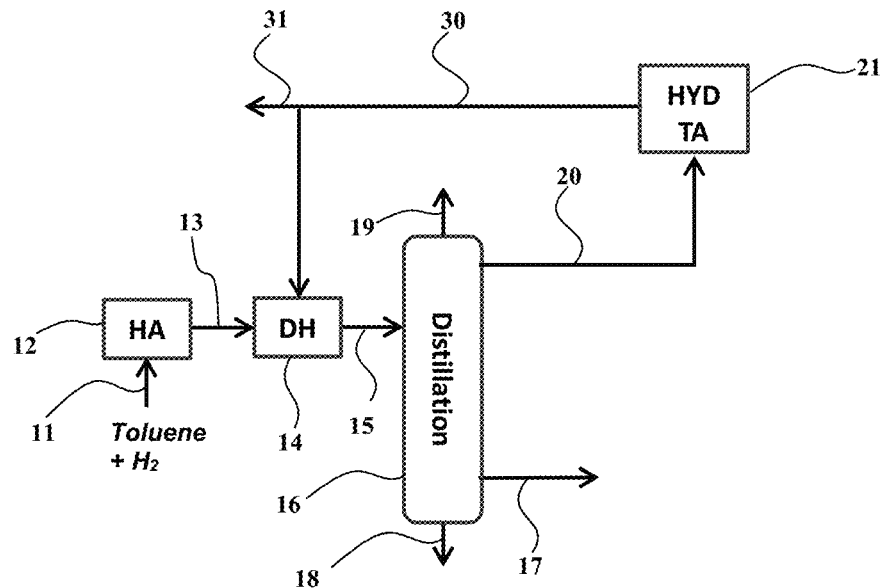
FIG. 1 is a flow diagram of a prior art process to produce DMBP isomers.

Before the present processes are disclosed and described, it is to be understood that unless otherwise indicated this disclosure is not limited to specific compositions, components, methods, or the like, as such may vary, unless otherwise specified. It is also to be understood that the terminology used herein is for the purpose of describing particular embodiments only and is not intended to be limiting.

It must also be noted that, as used in the specification and the appended claims, the singular forms 'a', 'an' and 'the' include plural referents unless otherwise specified. Thus, for example, reference to 'an alkaline earth' may include more than one alkaline earth, and the like.

Throughout this specification, use of the terms "comprises" or "comprising" or grammatical variations thereon shall be taken to specify the presence of stated features, integers, steps or components but does not preclude the presence or addition of one or more other features, integers, steps, components or groups thereof not specifically mentioned.

Described herein are advantageous processes for producing and separating DMBP isomers. In particular the disclosure provides processes for separating 2,X'-DMBP isomers from other hydrocarbons using at least one selective adsorption and then isomerizing the 2,X'-DMBP isomers to the more desirable 3,3'-, 3,4'- and 4,4'-DMBP isomers. The disclosure also provides processes for separating the dimethyl biphenyl isomers 3,3'-, 3,4'- and 4,4'-DMBP wherein the separation processes comprise at least one selective adsorption. The separation processes and isomerization processes may be integrated with DMBP production processes so as to provide processes which yield isomerically pure or substantially isomerically pure streams of each of 3,3'-3,4' or 4,4'-DMBP isomers. The separations may be facilitated by selective adsorption, particularly with zeolites or zeolite analogues.

In a first aspect of the present disclosure there is provided a process for separating one or more 2,X'-dimethyl biphenyl isomers (where X=2, 3 or 4) from a mixture comprising the same, the process comprising:

(g) contacting the mixture with a first adsorbent thereby selectively adsorbing one or more 2,X'-dimethyl biphenyl isomers (where X=2, 3 or 4) within said first adsorbent;

(h) withdrawing from said first adsorbent a first raffinate stream comprising one or more less selectively adsorbed components; and (i) withdrawing from said first adsorbent a first extract stream comprising said one or more selectively adsorbed 2,X'-dimethyl biphenyl isomers (where X=2, 3 or 4).

In a second aspect of the present disclosure there is provided a process for producing one or more 2,X'-dimethyl biphenyl isomers (where X=2, 3 or 4), the process comprising:

(d) contacting a feed comprising toluene with hydrogen in the presence of a hydroalkylation catalyst under conditions effective to produce a hydroalkylation reaction product comprising (methylcyclohexyl)toluenes;

(e) dehydrogenating at least part of the hydroalkylation reaction product in the presence of a dehydrogenation catalyst under conditions effective to produce a dehydrogenation reaction product comprising said dimethyl biphenyl isomers;

(f) separating the dehydrogenation reaction product into at least a first stream comprising one or more 3,3'-, 3,4'- and 4,4'-dimethyl biphenyl isomers and at least one second stream comprising one or more 2,X'-dimethyl biphenyl isomers (where X=2, 3 or 4);

(j) contacting the at least one second stream with a first adsorbent thereby selectively adsorbing one or more 2,X'-dimethyl biphenyl isomers (where X=2, 3 or 4) within said first adsorbent;

(k) withdrawing from said first adsorbent a first raffinate stream comprising one or more less selectively adsorbed components; and (l) withdrawing from said first adsorbent a first extract stream comprising one or more
selectively adsorbed 2,X'-dimethyl biphenyl isomers (where X=2, 3 or 4).

In a third aspect of the present disclosure there is provided a process for producing one or more 3,3'-, 3,4'- and 4,4'-dimethyl biphenyl isomers, the process comprising:

(h) contacting a feed comprising toluene with hydrogen in the presence of a hydroalkylation catalyst under conditions effective to produce a hydroalkylation reaction product comprising (methylcyclohexyl)toluenes;

(i) dehydrogenating at least part of the hydroalkylation reaction product in the presence of a dehydrogenation catalyst under conditions effective to produce a dehydrogenation reaction product comprising said dimethyl biphenyl isomers;

(j) separating the dehydrogenation reaction product into at least a first stream comprising one or more 3,3'-, 3,4'- and 4,4'-dimethyl biphenyl isomers and at least one second stream comprising one or more 2,X'-dimethyl biphenyl isomers (where X=2, 3 or 4);

(k) contacting the at least one second stream with a first adsorbent thereby selectively adsorbing one or more 2,X'-dimethyl biphenyl isomers (where X=2, 3 or 4) within the first adsorbent;

(l) withdrawing from said first adsorbent a first raffinate stream comprising one or more less selectively adsorbed components;

(m) withdrawing from said first adsorbent a first extract stream comprising one or more selectively adsorbed 2,X'-dimethyl biphenyl isomers (where X=2, 3 or 4);

(n) contacting said first extract stream with an isomerization catalyst under conditions effective to produce an isomerization effluent comprising one or more 3,3'-, 3,4'- or 4,4'-dimethyl biphenyl isomers.

In some embodiments at least a portion of the isomerization effluent formed in step (g) may be recycled to separation step (c).

The mixture of the first aspect or the second stream of either of the second or third aspects comprising the 2,X'-dimethyl biphenyl isomers, where X=2, 3 or 4, may comprise one or more of cyclopentadienyl toluenes (CPDTs), 4-methylcyclohexyl toluenes (4,X'-MCHTs, where X=2, 3 or 4), 3-methylcyclohexyl toluenes (3,X'-MCHTs, where X=2, 3 or 4), 2-methylcyclohexyl toluenes (2,X'-MCHTs, where X=2, 3, or 4), ethyl- or dimethyl-cyclopentyl toluenes (CPTs), 1-methylcyclohexyl toluenes (1,X'-MCHTs, where X=2, 3 or 4) and dimethyl bicyclohexanes (DMBCHs).

The use of a selective adsorption to separate the one or more 2,X'-dimethyl biphenyl (where X=2, 3 or 4) isomers from the MCHT components and other non-dimethyl biphenyl components is advantageous as it reduces the size of recycle loops and associated equipment.

In either of the second or third aspects the separation into at least a first stream and at least one second stream may comprise distillation and/or crystallization.

The process of the second or third aspect may further comprise the step of separating the 3,3'-, 3,4'- and 4,4'-dimethyl biphenyl isomers in the at least first stream, wherein said separation comprises at least one selective adsorption.

The separation of the 3,3'-, 3,4'- and 4,4'-dimethyl biphenyl isomers in the at least first stream may comprise:

(i) contacting the at least first stream with a second adsorbent thereby selectively adsorbing at least one of the 3,3'-, 3,4'- and 4,4'-dimethyl biphenyl isomers within said second adsorbent;

(ii) withdrawing from said second adsorbent a second raffinate stream comprising less selectively adsorbed 3,3'-, 3,4'- or 4,4'-dimethyl biphenyl isomers; and (iii) withdrawing from said second adsorbent a second extract stream comprising said selectively adsorbed 3,3'-, 3,4'- or 4,4'-dimethyl biphenyl isomers.

The separation of the 3,3'-, 3,4'- and 4,4'-dimethyl biphenyl isomers in the at least first stream may further comprise:

(i) contacting the second raffinate stream with a third adsorbent thereby selectively adsorbing one of the 3,3'-, 3,4'- or 4,4'-dimethyl biphenyl isomers less selectively adsorbed by the second adsorbent; and (ii) withdrawing from said third adsorbent a third extract stream comprising a less selectively adsorbed 3,3'-, 3,4'- or 4,4'-dimethyl biphenyl isomer and a fourth extract stream comprising said selectively adsorbed 3,3'-, 3,4'- or 4,4'-dimethyl biphenyl isomer.

The separation may further comprise selectively crystallizing one of the 3,3'-, 3,4'- or 4,4'-dimethyl biphenyl isomers from the second raffinate stream.

In either of the second or third aspects the separation of the 3,3'-, 3,4'- and 4,4'-dimethyl biphenyl isomers in the at least first stream may comprise:

(i) crystallizing at least one of the 3,3'-, 3,4'- or 4,4'-dimethyl biphenyl isomers to produce a product comprising that isomer and a third raffinate stream comprising non-crystallizing 3,3'-, 3,4'- and 4,4'-dimethyl biphenyl isomers;

(ii) contacting the third raffinate stream with a fourth adsorbent thereby selectively adsorbing at least one of the non-crystallizing 3,3'-, 3,4'- or 4,4'-dimethyl biphenyl isomers within the fourth adsorbent;

(iii) withdrawing from said fourth adsorbent a fourth raffinate stream comprising the less selectively adsorbed 3,3'-, 3,4'- or 4,4'-dimethyl biphenyl isomers; and (iv) withdrawing from said fourth adsorbent a fifth extract stream comprising said selectively adsorbed 3,3'-, 3,4'- or 4,4'-dimethyl biphenyl isomer.

The processes may further comprise the step of contacting at least part of any one or more of the second, third or fourth raffinate streams with an isomerization catalyst under conditions effective to produce an isomerization effluent comprising a mixture of dimethyl biphenyl isomers, wherein the relative ratios of the dimethyl biphenyl isomers after isomerization are different to the relative ratios prior to isomerization.

The processes may further comprise the step of contacting at least part of any one or more of the first to fifth extract streams with an isomerization catalyst under conditions effective to produce an isomerization effluent comprising a mixture of dimethyl biphenyl isomers, wherein the relative ratios of the dimethyl biphenyl isomers after isomerization are different to the relative ratios prior to isomerization.

The processes may further comprise the step of recycling at least part of the isomerization effluent from any one or more of the isomerization steps to the separation step of either of the second or third aspects which affords at least a first stream and at least one second stream.

The processes may further comprise the step of recycling at least part of the isomerization effluent from any one or more of the isomerization steps to any one or more of the adsorption steps and/or subjecting the mixture to crystallization to separate at least one of the 3,3'-3,4'- or 4,4'-dimethyl biphenyl isomers.

Any one or more of the herein disclosed selective adsorptions may be performed in the presence of one or more solvents. The solvent may comprise an aromatic hydrocarbon, a saturated hydrocarbon or combinations thereof.

The feed which is separated into at least a first stream comprising one or more 3,3'-, 3,4'- and 4,4'-dimethyl biphenyl isomers and at least one second stream comprising one or more 2,X'-dimethyl biphenyl isomers (where X=2, 3 or 4), may comprise 5-50% by weight 3,3'-isomer, 15-80% by weight 3,4'-isomer and 5-50% by weight 4,4'-isomer based on the total weight of the three isomers.

Any one or more of the isomerization effluents may comprise 10-60% by weight 3,3'-isomer, 10-60% by weight 3,4'-isomer, 2-30% by weight 4,4'-isomer and 2-30% by weight 2,X'-isomers (where X=2, 3 or 4) based on the total weight of the isomers.

Suitable isomerization catalysts include, but are not limited to, zeolites having a largest diffuse along diameter of 4.5 to 8 Å or greater than 4.8 Å.

In some embodiments the first raffinate stream of any of the first, second or third aspects may comprise one or more of cyclopentadienyl toluenes (CPDTs), 4-methylcyclohexyl toluenes (4,X'-MCHTs, where X=2, 3 or 4), 3-methylcyclohexyl toluenes (3,X'-MCHTs, where X=2, 3 or 4), 2-methylcyclohexyl toluenes (2,X'-MCHTs, where X=2, 3, or 4), ethyl- or dimethyl-cyclopentyl toluenes (CPTs), 1-methylcyclohexyl toluenes (1,X'-MCHTs, where X=2, 3 or 4) and dimethyl bicyclohexanes (DMBCHs).

In some embodiments at least a portion of the first raffinate stream of the second or third aspect may be recycled to dehydrogenation so as to dehydrogenate one or more of the 4-methylcyclohexyl toluenes (4,X'-MCHTs, where X=2, 3 or 4), 3-methylcyclohexyl toluenes (3,X'-MCHTs, where X=2, 3 or 4) and 2-methylcyclohexyl toluenes (2,X'-MCHTs, where X=2, 3, or 4) to their equivalent dimethyl biphenyl isomers.

In some embodiments at least a portion of the first raffinate stream of the second or third aspect may be recycled to hydroalkylation so as to transalkylate at least some of the 1-methylcyclohexyl toluenes (1,X'-MCHTs, where X=2, 3, or 4) to other methylcyclohexyl toluene isomers. These may then be sent to dehydrogenation to convert them to their equivalent dimethyl biphenyl isomers.

Any one or more of the selective adsorptions may comprise a simulated moving bed, membrane separation or semi-batch (swing) adsorption.

Any one or more of the selective adsorptions may be performed in a single vessel or, alternatively, in multiple vessels. Multiple vessels may be arranged in series or in parallel.

In some embodiments of the present disclosure any one or more of the first to fourth adsorbents may comprise a single adsorbent type designed to adsorb a particular dimethyl biphenyl isomer or isomers.

For example the first adsorbent may comprise an adsorbent designed to selectively adsorb any one or more of the 2,X'-dimethyl biphenyl isomers (where X=2, 3 or 4). In another example any one of the second to fourth adsorbents may comprise an adsorbent designed to selectively adsorb any one or more of the 3,3'-, 3,4'- and/or 4,4'-dimethyl biphenyl isomers.

In other embodiments any one or more of the adsorbents may comprise a mixture of more than one adsorbent types, the mixture being designed to selectively adsorb one or more dimethyl biphenyl isomers.

In some embodiments, when mixtures of more than one adsorbent type are utilized, the different adsorbent types may be located in a single vessel or in multiple vessels.

When located in a single vessel the different adsorbent types may be intimately mixed or, alternatively, may be layered so as to substantially separate one adsorbent type from another. Such layering may afford an effective series operation.

When located in multiple vessels, the vessels, and therefore the different adsorbent types, may be arranged in series or parallel.

In any of the herein disclosed processes the isolated, pure 3,3'-, 3,4'- and 4,4'-dimethyl biphenyl isomers may be subjected to oxidation to produce a dicarboxylic acid product.

The dicarboxylic acid may be reacted with a diol to produce a polyester product.

The carboxylic acid may be reacted with an alcohol to produce an esterification product.

Advantageously, as the 3,3'-, 3,4'- and 4,4'-dimethyl biphenyl isomers may be produced in high purity by the processes of the present disclosure, access to isomerically pure dicarboxylic acids and subsequent esterification products is possible.

Some embodiments of the present disclosure relate to the discovery that 2,X'-DMBP isomers (where X=2, 3 or 4) may be separated from other non-dimethyl biphenyl hydrocarbons utilizing selective adsorption, particularly using an adsorbent comprising metal cation treated zeolites. The separated 2,X'-dimethyl biphenyl isomers (where X=2, 3 or 4) may then be isomerized to the more desirable 3,3'-, 3,4'- and 4,4'-dimethyl biphenyl isomers. Such separation processes and isomerization processes may be integrated with dimethyl biphenyl production processes so as to provide processes which yield isomerically pure or substantially isomerically pure streams of each of 3,3'-, 3,4' or 4,4'-dimethyl biphenyl isomers. Separation of the 3,3'-, 3,4' or 4,4'-dimethyl biphenyl isomers may also be facilitated by selective adsorption, particularly with zeolites or zeolite analogues.

In some embodiments the adsorbent of the present disclosure is a zeolite or zeolite analogue.

As used herein the term 'zeolite', as well as encompassing aluminosilicate materials, also encompasses zeolite analogues where one or more of the framework aluminum or silicon atoms are replaced by another atom, such as, for example, boron, gallium, germanium, magnesium, titanium, phosphorus, nitrogen or sulfur.

Some embodiments of the present disclosure relate to the discovery that adsorbents comprising zeolites, wherein said zeolites comprise one or more metal cations in the +1 or +2 oxidation states, are capable of selectively adsorbing one or more of 2,X'-dimethyl biphenyl isomers (where X=2, 3 or 4) from mixtures thereof.

Some embodiments of the present disclosure relate to the discovery that adsorbents comprising zeolites, wherein said zeolites comprise one or more metal cations in the +1 or +2 oxidation states, are capable of selectively adsorbing one or more of 3,3'-, 3,4'- and 4,4'-dimethyl biphenyl isomers from mixtures thereof.

Other embodiments of the present disclosure relate to the discovery that adsorbents comprising zeolites, wherein said zeolites have a largest diffuse along dimension of at least about 4 Angstroms (Å), and wherein said zeolites are substantially free of metal cations in the +1 or +2 oxidation states, are capable of selectively adsorbing the 4,4'-dimethyl biphenyl isomer from mixtures of two or more of 3,3'-, 3,4'- and 4,4'-dimethyl biphenyl isomers.

As used herein the term 'largest diffuse along dimension' refers to a measure of the largest dimension of a zeolite channel system based on the diameter of the largest possible free-sphere that can diffuse along dimensions a, b or c of a zeolite channel and which are computed geometrically by Delaunay triangulation as detailed in: "A geometric solution to the largest-free-sphere problem in zeolite frameworks", M. D. Foster, I. Rivin, M. M. J. Treacy and O. Delgado Friedrichs, *Micropor. Mesopor. Mat.*, 90, 32-38, 2006.

Yet further embodiments of the present disclosure relate to the discovery that particular solvents, when utilized in any one or more of the herein disclosed adsorptive separations, enhance the selectivity for the adsorption of one or more dimethyl biphenyl isomers.

Metal Cation Containing Zeolites

In some embodiments the adsorbent is at least one zeolite, wherein said zeolite comprises one or more metal cations in the +1 or +2 oxidation states.

Said zeolite may have a largest diffuse along dimension of at least about 4 Angstroms (Å).

The largest diffuse along dimension of the zeolite may be at least about 4.5 Å, or at least about 5.0 Å, or at least about 5.5 Å, or at least about 6.0 Å, or at least about 6.5 Å, or at least about 7.0 Å.

The largest diffuse along dimension of the zeolite may be between about 4.0 Å and about 8.0 Å, or between about 4.5 Å and about 8.0 Å, or between about 5.0 Å and about 8.0 Å, or between about 5.5 Å and about 8.0 Å, or between about 6.0 Å and about 8.0 Å, or between about 6.5 Å and about 8.0 Å.

The zeolite structure type may comprise BEA, FAU, MFI, MEL, MTW, MOR, LTL, EMT, FER, MAZ, MEI, TON, MWW, EUO, MFS, IMF, MRE, ITN, MSE, MTT or IWV.

The zeolite may comprise a 12-ring zeolite, an 11-ring zeolite or a 10-ring zeolite.

The zeolite may comprise an X or Y type zeolite or a Beta type zeolite.

In some embodiments the Si/Al ratio of the zeolite may be less than about 200, or less than about 100, or less than about 50, or less than about 20, or less than about 10. The Si/Al ratio may preferably be less than 10.

In some embodiments the Si/Al ratio of the zeolite may be between about 1 and about 4, or between about 1.5 and about 3.5, or between about 2 and about 3.

The zeolite may comprise one or more alkali metal cations, alkaline earth metal cations, transition metal cations, rare earth metal cations or combinations thereof.

The zeolite may comprise one or more alkali metal cations, alkaline earth metal cations or combinations thereof.

The zeolite may comprise one or more of $Na+$, $K+$, $Rb+$, $Cs+$, $Mg2+$, $Ca2+$, $Sr2+$ and $Ba2+$ cations.

The zeolite may comprise one or more metal cations, wherein the ionic radius of the metal cation is between about 0.8 Å and about 2.0 Å.

In some embodiments the molar ratio of all metal cations in the +1 and/or +2 oxidation states relative to aluminum in the zeolite may be between about 0.01 and about 2.0, or between about 0.05 and about 1.5, or between about 0.1 and about 1.5, or between about 0.25 and about 1.5.

In some embodiments the molar ratio of all metal cations in the +1 and/or +2 oxidation states relative to aluminum in the zeolite may be greater than about 0.27, or greater than about 0.30, or greater than about 0.40, or greater than about 0.45, or greater than about 0.50.

In some embodiments the zeolites used to prepare the adsorbents of the present disclosure contain residual amounts of sodium cations. This is because the originally prepared zeolite may have used sodium containing compounds in its synthesis, for example in the case of a Y type zeolite. The amount of residual sodium cations may depend on the level of other metal cation exchange that has occurred during the cation exchange process.

In some embodiments the Na/Al molar ratio of the zeolite is less than about 1.0, or less than about 0.8, or less than about 0.6, or less than about 0.4, or less than about 0.3 when the zeolite contains at least one other metal cation.

In some embodiments the molar ratio of metal cations in the +1 and/or +2 oxidation states other than sodium and relative to aluminum in the zeolite may be greater than about 0.1, or greater than about 0.2, or greater than about 0.3, or greater than about 0.4. Preferably, the ratio is greater than about 0.3.

It has been discovered that the presence of particular metal cations facilitate selective adsorption of 2,X'-dimethyl biphenyl isomers (where X=2, 3 or 4) from non-DMBP compounds.

It has also been discovered that the presence of particular metal cations improve the separation of the 3,3'-, 3,4'- and 4,4'-dimethyl biphenyl isomers. The separation may be based on preferential adsorption of one or more of the 3,3'-, 3,4'- and 4,4'-dimethyl biphenyl isomers within the pores of the zeolite.

It has further been discovered that the crystallite size of the zeolite may improve the adsorptive ability. Accordingly, smaller crystallite size may improve adsorptive ability of the zeolite.

The average crystallite size of the zeolite may be less than about 5000 nm, or less than about 2000 nm, or less than about 1000 nm, or less than about 500 nm, or less than about 200 nm, or less than about 100 nm, or less than about 50 nm.

The average crystallite size of the zeolite may be from about 1 to about 5000 nm, or between about 1 and about 2000 nm, or from about 1 to about 1000 nm, or from about 5 to about 500 nm, or from about 10 to about 100 nm.

In some embodiments the processes disclosed herein comprise an adsorptive separation which separates 2,X'-dimethyl biphenyl isomers (where X=2, 3 or 4) from a mixture containing the same and wherein the mixture further comprises one or more non-DMBP compounds, as herein disclosed.

In some embodiments the processes disclosed herein comprise an adsorptive separation which separates 3,3'-DMBP from a mixture comprising two or more of 3,3'-DMBP, 3,4'-DMBP and 4,4'-DMBP.

In some embodiments the processes disclosed herein comprise an adsorptive separation which separates 3,4'-DMBP from a mixture comprising two or more of 3,3'-DMBP, 3,4'-DMBP and 4,4'-DMBP.

In some embodiments the processes disclosed herein comprise an adsorptive separation which separates 4,4'-DMBP from a mixture comprising two or more of 3,3'-DMBP, 3,4'-DMBP and 4,4'-DMBP.

In some embodiments the processes disclosed herein comprise an adsorptive separation which separates 2,X'-dimethyl biphenyl isomers (where X=2, 3 or 4) from a mixture containing the same, wherein the mixture further comprises one or more non-DMBP compounds as herein disclosed and the adsorbent comprises at least one zeolite, said zeolite comprising one or more metal cations in the +1 or +2 oxidation states.

In one embodiment the processes disclosed herein comprise an adsorptive separation which separates 3,3'-DMBP from a mixture comprising two or more of 3,3'-DMBP, 3,4'-DMBP and 4,4'-DMBP, wherein the adsorbent comprises at least one zeolite, said zeolite comprising one or more metal cations in the +1 or +2 oxidation states.

In one embodiment the processes disclosed herein comprise an adsorptive separation which separates 3,4'-DMBP from a mixture comprising two or more of 3,3'-DMBP, 3,4'-DMBP and 4,4'-DMBP, wherein the adsorbent comprises at least one zeolite, said zeolite comprising one or more metal cations in the +1 or +2 oxidation states.

In one embodiment the processes disclosed herein comprise an adsorptive separation which separates 4,4'-DMBP from a mixture comprising two or more of 3,3'-DMBP, 3,4'-DMBP and 4,4'-DMBP, wherein the adsorbent comprises at least one zeolite, said zeolite comprising one or more metal cations in the +1 or +2 oxidation states.

In other embodiments two or more different adsorbents which have different adsorption characteristics for each of the 2,X'-dimethyl biphenyl isomers (where X=2, 3 or 4) may be utilized. For example, two or three adsorbents in series operation.

A first selective adsorption may preferentially adsorb one of the 2,X'-dimethyl biphenyl isomers (where X=2, 3 or 4) and a second selective adsorption may preferentially adsorb one of the 2,X'-dimethyl biphenyl isomers (where X=2, 3 or 4) not preferentially adsorbed in the first selective adsorption.

A first selective adsorption may preferentially adsorb two of the 2,X'-dimethyl biphenyl isomers (where X=2, 3 or 4) and after desorption of these isomers, a second selective adsorption may preferentially adsorb one of them.

Accordingly, the use of two different adsorbents provides processes for separating 2,X'-dimethyl biphenyl isomers (where X=2, 3 or 4) from a mixture containing the same.

In other embodiments two different adsorbents which have different adsorption characteristics for the three DMBP isomers, 3,3'-DMBP, 3,4'-DMBP and 4,4'-DMBP, may be utilized. For example, two adsorbents in series operation.

A first selective adsorption may preferentially adsorb one of the 3,3'-, 3,4'- or 4,4'-dimethyl biphenyl isomers and a second selective adsorption may preferentially adsorb one of the 3,3'-, 3,4'- or 4,4'-dimethyl biphenyl isomers not preferentially adsorbed in the first selective adsorption.

A first selective adsorption may preferentially adsorb two of the 3,3'-, 3,4'- or 4,4'-dimethyl biphenyl isomers and after desorption of these isomers, a second selective adsorption may preferentially adsorb one of them.

Accordingly, the use of two different adsorbents provides processes for separating a mixture of the three 3,3'-, 3,4'- and 4,4'-dimethyl biphenyl isomers into pure components.

Substantially Metal Cation Free Zeolites

The adsorbent may comprise at least one zeolite, wherein said zeolite has a largest diffuse along dimension of at least about 4 Angstroms (Å).

The zeolite may be substantially free of alkali metal cations and alkaline earth metal cations. The alkali metal cation and alkaline earth metal cation content may, in combination, be less than about 0.1 wt. %, or less than about 0.075 wt. %, or less than about 0.05 wt. %.

The largest diffuse along dimension of the zeolite may be at least about 4.5 Å, or at least about 5.0 Å, or at least about 5.5 Å, or at least about 6.0 Å, or at least about 6.5 Å, or at least about 7.0 Å.

The largest diffuse along dimension of the zeolite may be between about 4.0 Å and about 8.0 Å, or between about 4.5 Å and about 8.0 Å, or between about 5.0 Å and about 8.0 Å, or between about 5.5 Å and about 8.0 Å, or between about 6.0 Å and about 8.0 Å, or between about 6.5 Å and about 8.0 Å.

Embodiments are directed to processes for separating 4,4'-DMBP from a mixture comprising 3,3'-DMBP, 3,4'-DMBP and 4,4'-DMBP. The mixture may be contacted under adsorption conditions with an adsorbent comprising, for example, ZSM-5 zeolite. Aspects of the disclosure are associated with the discovery that 'nano zeolites', for example, 'nano ZSM-5' (i.e., nano-size zeolite ZSM-5 crystallites having an average crystallite size below 1000 nm) provides highly advantageous performance characteristics when incorporated into adsorbents used in the adsorptive separation of 4,4'-DMBP. In particular, the mass transfer rate of 4,4'-DMBP into the zeolite pores is significantly greater, relative to zeolites synthesized according to conventional methods which typically have an average crystallite size on the order of 1-5 microns.

This increase in mass transfer rate in turn reduces the amount of adsorbent required to obtain a given flow rate of product (e.g., an extract product stream) from a given feed stream, for any desired set of performance parameters (e.g., 4,4'-DMBP purity and recovery). Process economics are therefore improved.

Adsorbents comprising 'nano-zeolites, for example 'nano ZSM-5', may have greater 4,4'-DMBP capacity with comparable selectivities, relative to zeolite adsorbents with larger average zeolite crystallite sizes.

The zeolite structure type may comprise BEA, FAU, MFI, MEL, MTW, MOR, LTL, EMT, FER, MAZ, MEI, TON, MWW, EUO, MFS, IMF, MRE, ITN, MTT, MSE or IWV.

The zeolite may comprise a 12-ring zeolite, an 11-ring zeolite or a 10-ring zeolite.

The zeolite may comprise a ZSM-5, or a ZSM-11, or a ZSM-57, or a ZSM-48 or a ZSM-12 type zeolite.

The zeolite may be a dealuminated zeolite or an aluminum free zeolite such as silicalite.

The Si/Al ratio of the zeolite may be greater than about 10, or greater than about 20, or greater than about 50, or greater than about 100, or greater than about 150, or greater than about 200.

The Si/Al ratio of the zeolite may be between about 10 and about 300 or between about 15 and about 250.

In another embodiment the process comprises an adsorptive separation which separates 4,4'-DMBP from a mixture comprising two or more of 3,3'-DMBP, 3,4'-DMBP and 4,4'-DMBP wherein the adsorbent comprises one or more zeolites, said zeolite having an average crystallite size between 1 and 100 nm, and said zeolite being substantially free of metal cations in the +1 or +2 oxidation states.

Solvent Effects

Aspects of the present disclosure are based on the surprising discovery that solvent choice may improve the separation of particular DMBP isomers.

In some embodiments, the solvent may be the non-DMBP components in a given mixture. For example, in the selective adsorption of 2,X'-dimethyl biphenyl isomers (where X=2, 3 or 4) the MCHT components, and/or other non-DMBP components, may serve as a solvent. In other embodiments it may be advantageous to add a further solvent.

In some embodiments of the processes of the present disclosure the degree of separation of DMBP isomers, either from non-DMBP components or from each other, may be based on the kinetic diameter of the solvent. The kinetic diameter may be derived from a spherical model or a smallest ellipsoid model. In other embodiments the degree of separation may be based on the polarity of the solvent. In yet other embodiments the degree of separation may be based on both the kinetic diameter of the solvent and its polarity. Accordingly, solvents which are bulkier (generally a larger kinetic diameter) may afford improved separation of the isomers, however this effect may be modulated by solvent polarity. Generally, single ring aromatic solvents such as benzene adsorb to the zeolite more strongly that saturated solvents.

Without wishing to be bound by theory it is believed that there is a tertiary interaction involving the DMBP isomers, the solvent and the zeolite pores which impact on the efficacy of selective adsorption of one or more of the DMBP isomers. Preferred solvents are those which do not significantly compete with a particular DMBP isomer in respect of adsorption into the pores of the zeolite. Accordingly, due to their higher polarity, aromatic solvents are more likely to be bulkier relative to aliphatic solvents to achieve comparable adsorption of a DMBP isomer.

The kinetic diameters of various solvents of relevance to the present disclosure are shown in Table 2 below (see J.

Chem. Soc., Faraday Trans., 1996, 92, 2499-2502 and J. Phys. Chem, 1996, 100, 7676-7679).

TABLE 2

| Solvent | Kinetic Diameter (Å) |
|---|---|
| iso-octane | 6.2 |
| tri-isopropyl benzene | 8.5 |
| toluene | 5.9 |
| p-xylene | 5.9 |
| m-xylene | 6.8 |
| mesitylene | 7.5 |

In some embodiments the solvent comprises a saturated organic solvent wherein the kinetic diameter of the solvent is greater than about 4.5 Å, or greater than about 5.0 Å, or greater than about 5.5 Å, or greater than about 6.0 Å.

In some embodiments the solvent comprises an aromatic organic solvent wherein the kinetic diameter of the solvent is greater than about 6.0 Å, or greater than about 6.5 Å, or greater than about 7.0 Å, or greater than about 7.5 Å.

In one embodiment the process comprises an adsorptive separation which separates one or more 2,X'-DMBP isomers (where X=2, 3 or 4) from non-DMBP components, particularly one or more MCHTs, wherein the adsorbent comprises at least one zeolite, said zeolite comprising one or more alkali metal cations, one or more alkaline earth cations or combinations thereof, said metal cations being in the +1 or +2 oxidation states.

In another embodiment the process comprises an adsorptive separation which separates one or more 2,X'-DMBP isomers (where X=2, 3 or 4) from non-DMBP components, particularly one or more MCHTs, wherein the adsorbent comprises at least one zeolite, said zeolite comprising barium cations.

In another embodiment the process comprises an adsorptive separation which separates one or more 2,X'-DMBP isomers (where X=2, 3 or 4) from non-DMBP components, particularly one or more MCHTs, wherein the adsorbent comprises at least one zeolite, wherein said zeolite comprises barium cations and wherein the solvent comprises iso-octane.

In another embodiment the process comprises and adsorptive separation which separates one or more 2,X'-DMBP isomers (where X=2, 3 or 4) from non-DMBP components, particularly one or more MCHTs, wherein the adsorbent comprises at least one zeolite, said zeolite comprising potassium cations.

In another embodiment the process comprises an adsorptive separation which separates one or more 2,X'-DMBP isomers (where X=2, 3 or 4) from non-DMBP components, particularly one or more MCHTs, wherein the adsorbent comprises at least one zeolite, said zeolite comprising potassium cations and wherein the solvent comprises 1,3,5-trimethylbenzene.

In another embodiment the process comprises an adsorptive separation which separates one or more 2,X'-DMBP isomers (where X=2, 3 or 4) from non-DMBP components, particularly one or more MCHTs, wherein the adsorbent comprises one or more zeolites, said zeolite comprising cesium cations.

In another embodiment the process comprises an adsorptive separation which separates one or more 2,X'-DMBP isomers (where X=2, 3 or 4) from non-DMBP components, particularly one or more MCHTs, wherein the adsorbent comprises at least one zeolite, said zeolite comprising cesium cations and wherein the solvent comprises iso-octane.

In another embodiment the process comprises an adsorptive separation which separates one or more 2,X'-DMBP isomers (where X=2, 3 or 4) from non-DMBP components, particularly one or more MCHTs, wherein the adsorbent comprises at least one zeolite, said zeolite comprising a Beta zeolite and potassium cations.

In one embodiment the process comprises separating one or more 2,X'-DMBP isomers (where X=2, 3 or 4) from non-DMBP components, particularly one or more MCHTs, wherein the zeolite has a largest diffuse along dimension of at least about 4 Angstroms (Å).

In one embodiment the process comprises separating one or more 2,X'-DMBP isomers (where X=2, 3 or 4) from non-DMBP components, particularly one or more MCHTs, wherein the zeolite has a largest diffuse along dimension of at least about 4 Angstroms (Å), and wherein the solvent is a saturated organic solvent having a kinetic diameter greater than about 4.5 Å.

In another embodiment the process comprises separating one or more 2,X'-DMBP isomers (where X=2, 3 or 4) from non-DMBP components, particularly one or more MCHTs, wherein the zeolite has a largest diffuse along dimension of at least about 4 Angstroms (Å), and wherein the solvent is an aromatic organic solvent having a kinetic diameter greater than about 6.0 Å.

In another embodiment the process comprises separating one or more 2,X'-DMBP isomers (where X=2, 3 or 4) from non-DMBP components, particularly one or more MCHTs, wherein the zeolite has a largest diffuse along dimension of at least about 4 Angstroms (Å), and wherein the average crystallite size of the zeolite is from about 10 to about 100 nm.

In another embodiment the process comprises separating one or more 2,X'-DMBP isomers (where X=2, 3 or 4) from non-DMBP components, particularly one or more MCHTs, wherein the zeolite has a largest diffuse along dimension of at least about 4 Angstroms (Å), wherein the average crystallite size of the zeolite is from about 10 to about 100 nm, and wherein the solvent is a saturated organic solvent having a kinetic diameter greater than about 4.5 Å.

In another embodiment the process comprises separating one or more 2,X'-DMBP isomers (where X=2, 3 or 4) from non-DMBP components, particularly one or more MCHTs, wherein the zeolite has a largest diffuse along dimension of at least about 4 Angstroms (Å), wherein the average crystallite size of the zeolite is from about 10 to about 100 nm, and wherein the solvent is a an aromatic organic solvent having a kinetic diameter greater than about 6.0 Å.

In another embodiment the process comprises separating one or more 2,X'-DMBP isomers (where X=2, 3 or 4) from non-DMBP components, particularly one or more MCHTs, wherein the zeolite has a largest diffuse along dimension of at least about 4 Angstroms (Å), wherein the average crystallite size of the zeolite is from about 10 to about 100 nm, and wherein the solvent comprises iso-octane, m-xylene, 1,2,4-trimethylbenzene, 1,3,5-trimethylbenzene, 1,4-diisopropylbenzene, 3,3'-DMBP, 1,3,5-triisopropylbenzene or combinations thereof.

In one embodiment the process comprises an adsorptive separation which separates 3,3'-DMBP from a mixture comprising two or more of 3,3'-DMBP, 3,4'-DMBP and 4,4'-DMBP, wherein the adsorbent comprises at least one zeolite, said zeolite comprising one or more alkali metal cations, one or more alkaline earth cations or combinations thereof, said metal cations being in the +1 or +2 oxidation states.

In another embodiment the process comprises an adsorptive separation which separates 3,3'-DMBP from a mixture comprising two or more of 3,3'-DMBP, 3,4'-DMBP and 4,4'-DMBP, wherein the adsorbent comprises at least one zeolite, said zeolite comprising barium cations.

In another embodiment the process comprises an adsorptive separation which separates 3,3'-DMBP from a mixture comprising two or more of 3,3'-DMBP, 3,4'-DMBP and 4,4'-DMBP, wherein the adsorbent comprises at least one zeolite, wherein said zeolite comprises barium cations and wherein the solvent comprises iso-octane.

In one embodiment the process comprises an adsorptive separation which separates 3,4'-DMBP from a mixture comprising two or more of 3,3'-DMBP, 3,4'-DMBP and 4,4'-DMBP, wherein the adsorbent comprises at least one zeolite, said zeolite comprising one or more alkali metal cations, one or more alkaline earth cations or combinations thereof, said metal cations being in the +1 or +2 oxidation states.

In another embodiment the process comprises and adsorptive separation which separates 3,4'-DMBP from a mixture comprising two or more of 3,3'-DMBP, 3,4'-DMBP and 4,4'-DMBP, wherein the adsorbent comprises at least one zeolite, said zeolite comprising potassium cations.

In another embodiment the process comprises an adsorptive separation which separates 3,4'-DMBP from a mixture comprising two or more of 3,3'-DMBP, 3,4'-DMBP and 4,4'-DMBP, wherein the adsorbent comprises at least one zeolite, said zeolite comprising potassium cations and wherein the solvent comprises 1,3,5-trimethylbenzene.

In one embodiment the process comprises an adsorptive separation which separates 4,4'-DMBP from a mixture comprising two or more of 3,3'-DMBP, 3,4'-DMBP and 4,4'-DMBP, wherein the adsorbent comprises at least one zeolite, said zeolite comprising one or more alkali metal cations, one or more alkaline earth cations or combinations thereof, said metal cations being in the +1 or +2 oxidation states.

In another embodiment the process comprises an adsorptive separation which separates 4,4'-DMBP from a mixture comprising two or more of 3,3'-DMBP, 3,4'-DMBP and 4,4'-DMBP wherein the adsorbent comprises one or more zeolites, said zeolite comprising cesium cations.

In another embodiment the process comprises an adsorptive separation which separates 4,4'-DMBP from a mixture comprising two or more of 3,3'-DMBP, 3,4'-DMBP and 4,4'-DMBP wherein the adsorbent comprises at least one zeolite, said zeolite comprising cesium cations and wherein the solvent comprises iso-octane.

In another embodiment the process comprises an adsorptive separation which separates 4,4'-DMBP from a mixture comprising two or more of 3,3'-DMBP, 3,4'-DMBP and 4,4'-DMBP wherein the adsorbent comprises at least one zeolite, said zeolite comprising a Beta zeolite and potassium cations.

In some embodiments the processes disclosed herein comprise separating 4,4'-DMBP from a mixture comprising two or more of 3,3'-DMBP, 3,4'-DMBP and 4,4'-DMBP.

In one embodiment the process comprises separating 4,4'-DMBP from a mixture comprising two or more of 3,3'-DMBP, 3,4'-DMBP and 4,4'-DMBP, wherein the zeolite has a largest diffuse along dimension of at least about 4 Angstroms (Å).

In one embodiment the process comprises separating 4,4'-DMBP from a mixture comprising 3,3'-DMBP, 3,4'-DMBP and 4,4'-DMBP, wherein the zeolite has a largest diffuse along dimension of at least about 4 Angstroms (Å), and wherein the solvent is a saturated organic solvent having a kinetic diameter greater than about 4.5 Å.

In another embodiment the process comprises separating 4,4'-DMBP from a mixture comprising 3,3'-DMBP, 3,4'-DMBP and 4,4'-DMBP, wherein the zeolite has a largest diffuse along dimension of at least about 4 Angstroms (Å), and wherein the solvent is an aromatic organic solvent having a kinetic diameter greater than about 6.0 Å.

In another embodiment the process comprises separating 4,4'-DMBP from a mixture comprising 3,3'-DMBP, 3,4'-DMBP and 4,4'-DMBP, wherein the zeolite has a largest diffuse along dimension of at least about 4 Angstroms (Å), and wherein the average crystallite size of the zeolite is from about 10 to about 100 nm.

In another embodiment the process comprises separating 4,4'-DMBP from a mixture comprising 3,3'-DMBP, 3,4'-DMBP and 4,4'-DMBP, wherein the zeolite has a largest diffuse along dimension of at least about 4 Angstroms (Å), wherein the average crystallite size of the zeolite is from about 10 to about 100 nm, and wherein the solvent is a saturated organic solvent having a kinetic diameter greater than about 4.5 Å.

In another embodiment the process comprises separating 4,4'-DMBP from a mixture comprising 3,3'-DMBP, 3,4'-DMBP and 4,4'-DMBP, wherein the zeolite has a largest diffuse along dimension of at least about 4 Angstroms (Å), wherein the average crystallite size of the zeolite is from about 10 to about 100 nm, and wherein the solvent is a an aromatic organic solvent having a kinetic diameter greater than about 6.0 Å.

In another embodiment the process comprises separating 4,4'-DMBP from a mixture comprising 3,3'-DMBP, 3,4'-DMBP and 4,4'-DMBP, wherein the zeolite has a largest diffuse along dimension of at least about 4 Angstroms (Å), wherein the average crystallite size of the zeolite is from about 10 to about 100 nm, and wherein the solvent comprises iso-octane, m-xylene, 1,2,4-trimethylbenzene, 1,3,5-trimethylbenzene, 1,4-diisopropylbenzene, 3,3'-DMBP, 1,3,5-triisopropylbenzene or combinations thereof.

In some embodiments the solvent heat of adsorption is less than a DMBP isomer heat of adsorption.

In some embodiments mixtures of solvents may be utilized to facilitate adsorptive separation of the DMBP isomers. In other embodiments solvent gradients may be utilized to improve separation.

In some embodiments two or more different adsorbents which have different adsorption characteristics for each of the 2,X'-dimethyl biphenyl isomers (where X=2, 3 or 4) may be utilized. For example, two or more adsorbents in series operation. These separations may be performed in the presence of the same or different solvents.

For example, a first selective adsorption may preferentially adsorb one of the 2,X'-dimethyl biphenyl isomers (where X=2, 3 or 4) in the presence of a first solvent and a second selective adsorption may preferentially adsorb one of the 2,X'-dimethyl biphenyl isomers (where X=2, 3 or 4) not preferentially adsorbed in the first selective adsorption and in the presence of a second solvent, which may be the same or different to the first solvent.

A first selective adsorption may preferentially adsorb two of the 2,X'-dimethyl biphenyl isomers (where X=2, 3 or 4) in the presence of a first solvent and after desorption of these isomers a second selective adsorption may preferentially adsorb one of them, and in the presence of a second solvent which may be the same or different to the first solvent.

Accordingly, the use of two different adsorbents either in the presence of the same or different solvents provides a process for separating the 2,X'-dimethyl biphenyl isomers (where X=2, 3 or 4) from non-DMBP components.

In other embodiments two different adsorbents which have different adsorption characteristics for the 3,3'-DMBP, 3,4'-DMBP and 4,4'-DMBP isomers may be utilized. For example, two adsorbents in series operation. These separations may be performed in the presence of the same or different solvents.

For example, a first selective adsorption may preferentially adsorb one of the 3,3'-, 3,4'- or 4,4'-dimethyl biphenyl isomers in the presence of a first solvent and a second selective adsorption may preferentially adsorb one of the 3,3'-, 3,4'- or 4,4'-dimethyl biphenyl isomers not preferentially adsorbed in the first selective adsorption and in the presence of a second solvent, which may be the same or different to the first solvent.

A first selective adsorption may preferentially adsorb two of the 3,3'-, 3,4'- or 4,4'-dimethyl biphenyl isomers in the presence of a first solvent and after desorption of these isomers a second selective adsorption may preferentially adsorb one of them, and in the presence of a second solvent which may be the same or different to the first solvent.

Accordingly, the use of two different adsorbents either in the presence of the same or different solvents provides a process for separating a mixture of the three DMBP isomers into pure components.

In some embodiments, the solvent or solvents used in the adsorptive separations may have a boiling point that is substantially lower than those of the DMBP isomers and MCHT isomers to facilitate separation of the solvents from the DMBP isomers and MCHT isomers by, for example, fractional distillation. In other embodiments a solvent of higher boiling point than those of the DMBP isomers and MCHT isomers may be utilized. Both solvents of higher and lower boiling points to those of the DMBP isomers and MCHT isomers may be utilized. In some embodiments the difference between the boiling point of the solvent or solvents and the boiling point of any one of the DMBP isomers or MCHT isomers is greater than about 100° C., or greater than about 75° C., or greater than about 50° C., or greater than about 25° C.

The person of ordinary skill in the art will appreciate that through selection of zeolite adsorbent combinations, separation of 2,X'-dimethyl biphenyl isomers (where X=2, 3 or 4) from non-DMBP components may be achieved.

The person of ordinary skill in the art will also appreciate that through selection of zeolite adsorbent combinations, separation of all three of 3,3'-DMBP, 3,4'-DMBP and 4,4'-DMBP may be achieved.

The processes of the present disclosure may afford pure, substantially pure or enriched individual DMBP isomers. Purities of 3,3'-DMBP, 3,4'-DMBP and 4,4'-DMBP may, independently, be greater that about 90 wt. %, or greater than about 95 wt. %, or greater than about 96 wt. %, or greater than about 97 wt. % or greater than about 98 wt. %, or greater than about 99 wt. % or greater than about 99.5 wt. % or greater than about 99.9 wt. %.

The adsorptive separations may be performed over a wide range of temperatures. Preferably the temperature is above about 20° C., more preferably above about 115° C. The temperature may be between about 20° C. and about 300° C., or between about 20° C. and about 250° C., or between about 20° C. and about 200° C.

The adsorptive separations may be performed in batch or continuous mode.

The contact time between the adsorbent and the dimethyl biphenyl isomer mixture may be between a few seconds and several hours, or between a few minutes and several hours, or between about 0.5 hours and about 10 hours, or between about 0.5 hours and about 5 hours.

Production of Dimethyl-Substituted Biphenyl Compounds from Toluene

Exemplary production methods for dimethyl biphenyl compounds are disclosed in WO 2015/112252 the entire contents of which are incorporated by reference herein.

In one embodiment the feed employed in the presently disclosed process comprises toluene, which is initially converted to (methylcyclohexyl)toluenes by reaction with hydrogen over a hydroalkylation catalyst.

At least a portion of the hydroalkylation reaction effluent, comprising (methylcyclohexyl)toluenes, is then dehydrogenated to convert the (methylcyclohexyl)toluenes to the corresponding dimethyl biphenyl compounds.

The product of the dehydrogenation step comprises dimethyl biphenyl compounds in which the concentration of the 3,3'-, 3,4'- and 4,4'-isomers is at least 50 wt %, or at least 60 wt %, or at least 70 wt % based on the total weight of dimethyl biphenyl compounds. Typically, the concentration of the 2,X'-dimethylbiphenyl isomers in the dehydrogenation product is less than 50 wt %, or less than 30 wt %, or from 5 to 25 wt % based on the total weight of dimethyl biphenyl compounds.

Separation of 3,3', 3,4' and 4,4'-Dimethyl Biphenyl Isomers

Depending on the intended use of the dimethyl biphenyl isomer, it is desirable to provide a simple and effective method of separating and recovering each of the 3,3', 3,4' and 4,4' dimethyl biphenyl isomers and, in some embodiments, mixtures of two isomers. In addition, it may be desirable to convert some or all the remaining 2,X' (where X is 2, 3 or 4) dimethyl biphenyl isomers into the more desirable 3,Y' (where Y is 3 or 4) and 4,4'-dimethyl biphenyl isomers.

Irrespective of the process used, the raw dimethyl biphenyl product from the production sequences described herein will contain unreacted components and by-products in addition to a mixture of dimethyl biphenyl isomers. For example, where the initial feed comprises toluene and the production sequence involves hydroalkylation to MCHT and dehydrogenation of the MCHT, the raw dimethyl biphenyl product will tend to contain residual toluene and MCHT and by-products including hydrogen, methylcyclohexane, dimethylcyclohexylbenzene, and heavy hydrocarbons in addition to the target dimethyl biphenyl isomers. Thus, in some embodiments, prior to any separation of the dimethyl biphenyl isomers, the raw product of the MCHT dehydrogenation is subjected to an initial separation to remove at least part of the residues and by-products with significantly different boiling points from the dimethyl biphenyl isomers. For example, the hydrogen by-product can be removed and recycled to the hydroalkylation and/or MCHT dehydrogenation steps, while residual toluene and methylcyclohexane by-product can be removed and recycled to the hydroalkylation step. Similarly, part of the heavy components can be removed in an initial separation and can be recovered for use as a fuel or can be reacted with toluene over a transalkylation catalyst to convert some of the dialkylate to additional MCHT. A suitable initial separation can be achieved by one or more distillations.

Table 3 depicts the structures of various components that the raw product of MCHT dehydrogenation may comprise in addition to 3,3'-DMBP, 3,4'-DMBP and 4,4'-DMBP. As will be appreciated, numerous regioisomers of the components are possible.

TABLE 3

| Structure | Name |
|---|---|
| DMBCHs | dimethyl bicyclohexanes |
| 1,X'-MCHTs | 1-methylcyclohexyl toluenes |
| CPTs | ethyl cyclopentyl toluenes or dimethyl cyclopentyl toluenes |
| 2,X'-MCHTs | 2-methylcyclohexyl toluenes |
| 3,X'-MCHTs | 3-methylcyclohexyl toluenes |
| 4,X'-MCHTs | 4-methylcyclohexyl toluenes |
| CPDTs | cyclopentadienyl toluenes |
| 2,2'-DMBP | 2,2-dimethyl biphenyl |
| 2,3'-DMBP | 2,3-dimethyl biphenyl |
| 2,4'-DMBP | 2,4-dimethyl biphenyl |

Conversion of 2,X'-Dimethyl Biphenyl Isomers

Part or all of the 2,X'-dimethyl biphenyl (DMBP) isomers in the second stream described above, can be processed to increase the concentration of 3,3'-, 3,4' and 4,4' dimethyl biphenyl (DMBP) in the second stream. One suitable process comprises a combination of hydrogenation of the DMBP back to MCHT, followed by transalkylation of the MCHT with toluene and then dehydrogenation of the transalkylation product back to DMBP. In some embodiments the hydrogenation unit and transalkylation unit can be combined as a single reactor. Such a process is described in WO 2015/191289 the entire contents of which are incorporated by reference herein. In particular, it is found that steric issues favor the transalkylation of 2-methylcyclohexyl toluenes to 3- and 4-methylcyclohexyl toluenes.

A feature of the processes of the present disclosure is replacement of the hydrogenation/transalkylation process step(s) with an adsorptive separation step in which 2,X'-DMBP isomers are separated from other hydrocarbon compounds. An advantage of this is that hydrogenation/transalkylation may have relatively low selectivity which increases the size of the transalkylation loop and associated equipment. Using an adsorptive process the separated 2,X'-DMBPs may be sent directly to isomerization where, in some embodiments, they are converted to a mixture of DMBP isomers, thus increasing the overall amounts of desired 3,3'-, 3,4'- and 4,4'-DMBP isomers in the process. In one embodiment non-DMBP hydrocarbons may be sent back to dehydrogenation if the stream contains significant amounts of MCHTs that can be dehydrogenated to DMBP. In another embodiment this stream may be purged to remove the CPTs and 1,X'-MCHTs that cannot be converted to DMBP. In an alternate embodiment this stream may be at least partially recycled to the hydroalkylation unit to allow 1,X'-MCHTs to transalkylate to other MCHT isomers which may then be dehydrogenated to DMBP.

The adsorptive separation may or may not require added solvent. The by-product mixture comprising CPTs and MCHTs may also perform well as the solvent carrier. The selective adsorption functions so as to separate all undesired DMBP isomers from the CPTs/MCHTs so that they can be isomerized into more of the desired product.

The disclosure will now be more particularly described with reference to the following non-limiting examples and FIGS. 1 to 23 of the accompanying drawings.

FIG. 1 illustrates a prior art process for the production of DMBP isomers (see WO 2015/191289) in which toluene and hydrogen are fed by a single line 11 or, if preferred by separate lines (not shown), to a hydroalkylation unit 12. The hydroalkylation unit 12 contains a bed of a bifunctional catalyst which comprises a hydrogenation component and a solid acid alkylation component and which converts the toluene to (methylcyclohexyl)toluene (MCHT). The effluent from the hydroalkylation unit 12, composed mainly of MCHT and unreacted toluene, is then fed via line 13 to a dehydrogenation unit 14 where the MCHT is dehydrogenated to produce dimethyl biphenyl (DMBP) and hydrogen.

The effluent from the dehydrogenation unit 14 is then supplied by line 15 to a DMBP recovery system 16, including one or more distillation columns, where a light fraction is removed via line 19, and optionally recycled in part. Also removed from the dehydrogenation effluent by DMBP recovery system 16 are a first intermediate stream rich in 3,3'-, 3,4'- and 4,4'-DMBP isomers, which is recovered as product via line 17, and a second intermediate stream rich in 2,X'-DMBP isomers and residual MCHT, which is removed via line 20. Heavies are collected in line 18 and optionally recovered for use as fuel or as feedstock to other chemical processes.

The second intermediate stream, rich in 2,X'-DMBP isomers and residual MCHT, is supplied by line 20 to a hydrogenation/transalkylation unit and finally to the dehydrogenation unit. The hydrogenation unit converts the 2,X'-DMBP isomers back to the corresponding MCHT isomers, then the transalkylation unit reacts the MCHT with toluene to produce a transalkylation product having a different MCHT isomer distribution to the hydrogenation product. The dehydrogenation unit then converts the MCHT in the transalkylation product to DMBP having a different isomer distribution than that in line 20. The hydrogenation unit and the transalkylation unit can be combined as a single reactor.

Figure 2:
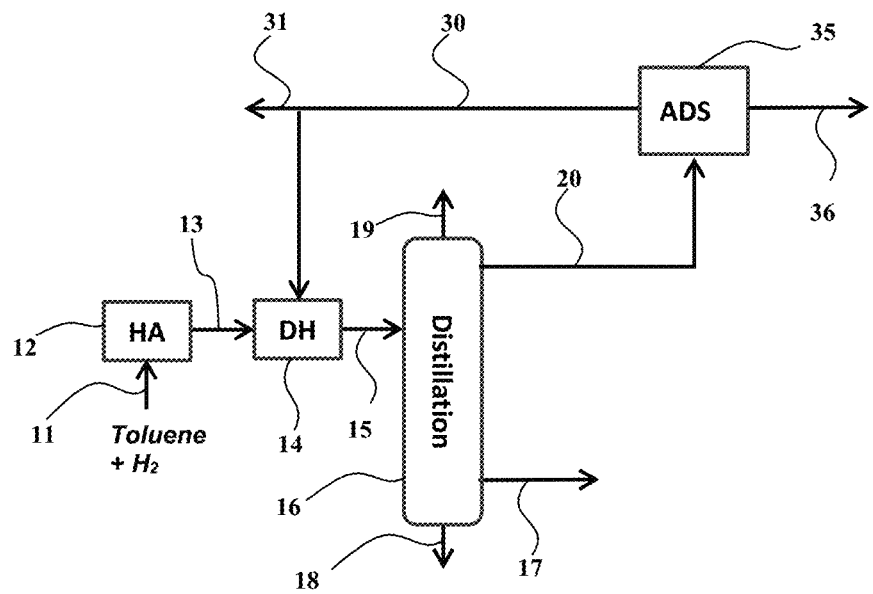
FIG. 2 is a flow diagram of a process for producing DMBP isomers from toluene according to one embodiment of the present disclosure.

An embodiment of a process according to the present disclosure for producing DMBP isomers from a toluene-containing feed is illustrated in FIG. 2, in which toluene and hydrogen are fed by a single line 11 or, if preferred by separate lines (not shown), to a hydroalkylation unit 12. The hydroalkylation unit 12 contains a bed of a bifunctional catalyst which comprises a hydrogenation component and a solid acid alkylation component and which converts at least part of the toluene to (methylcyclohexyl)toluene (MCHT). The effluent from the hydroalkylation unit 12, comprising MCHT and unreacted toluene is then fed via line 13 to a dehydrogenation unit 14 where the MCHT is dehydrogenated to produce dimethylbiphenyl (DMBP) and hydrogen.

The effluent from the dehydrogenation unit 14 is then fed via line 15 to a distillation unit 16, where the 3,3', 3,4'- and 4,4'-DMBP isomers are separated and removed via line 17. More volatile unreacted MCHT and 2,X'-DMBP isomers are separated and removed via line 20. A heavy fraction is removed via line 18 and a light fraction via line 19.

Stream 20 is sent to a selective adsorption unit, which may comprise one or more adsorption steps and/or adsorbent types which selectively adsorbs the 2,X'-DMBP isomers which are then recovered via extract stream 36.

The other hydrocarbons in stream 20 are not adsorbed and exit the unit as raffinate stream via line 30 which is supplied to the dehydrogenation unit. Residual MCHT in stream 30 is converted to DMBP in the dehydrogenation unit. Optionally, purge line 31 removes 1,X'-MCHT isomers and CPTs. In an alternate embodiment this stream may be at least partially recycled to the hydroalkylation unit to allow 1,X'-MCHTs to transalkylate to other MCHT isomers which may then be dehydrogenated to DMBP.

Figure 3:
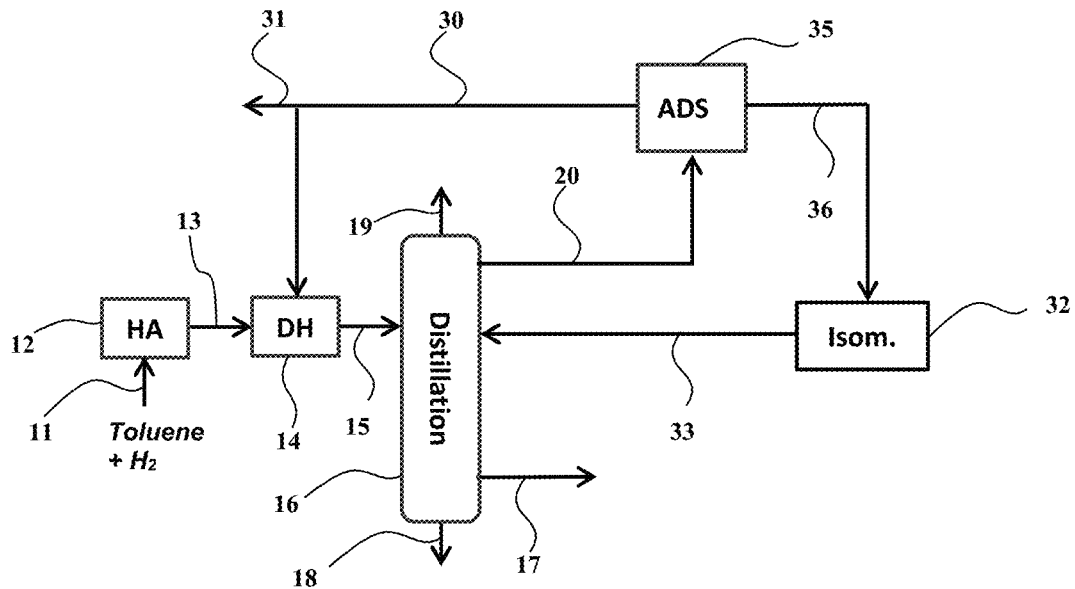
FIG. 3 is a flow diagram of a process for producing DMBP isomers from toluene according to one embodiment of the present disclosure.

Another embodiment of a process for producing DMBP isomers from a toluene-containing feed is illustrated in FIG. 3, in which toluene and hydrogen are fed by a single line 11 or, if preferred by separate lines (not shown), to a hydroalkylation unit 12. The hydroalkylation unit 12 contains a bed of a bifunctional catalyst which comprises a hydrogenation component and a solid acid alkylation component and which converts at least part of the toluene to (methylcyclohexyl)toluene (MCHT). The effluent from the hydroalkylation unit 12, comprising MCHT and unreacted toluene is then fed via line 13 to a dehydrogenation unit 14 where the MCHT is dehydrogenated to produce dimethylbiphenyl (DMBP) and hydrogen.

The effluent from the dehydrogenation unit 14 is then fed via line 15 to a distillation unit 16, where the 3,3', 3,4'- and 4,4'-DMBP isomers are separated and removed via line 17. More volatile unreacted MCHT and 2,X'-DMBP isomers are separated and removed via line 20. A heavy fraction is removed via line 18 and a light fraction via line 19.

Stream 20 is sent to a selective adsorption unit, which may comprise one or more adsorption steps, and/or adsorbent types, which selectively adsorbs the 2,X'-DMBP isomers which are then recovered via extract stream 36. The extract stream 36 is then sent to isomerization unit 32, which affords a mixture of DMBP isomers. The effluent from the isomerization unit is fed via line 33 to the distillation unit. This process increases the overall amount of desirable 3,3'-, 3,4'- and 4,4'-DMBP isomers.

The other hydrocarbons in stream 20 are not adsorbed and exit the adsorption unit 35 as raffinate stream 30 which is supplied to the dehydrogenation unit. Residual MCHT in stream 30 is converted to DMBP in the dehydrogenation unit. Optionally, purge line 31 removes 1,X'-MCHT isomers and CPTs. In an alternate embodiment this stream may be at least partially recycled to the hydroalkylation unit to allow 1,X'-MCHTs to transalkylate to other MCHT isomers which may then be dehydrogenated to DMBP.

Figure 4:
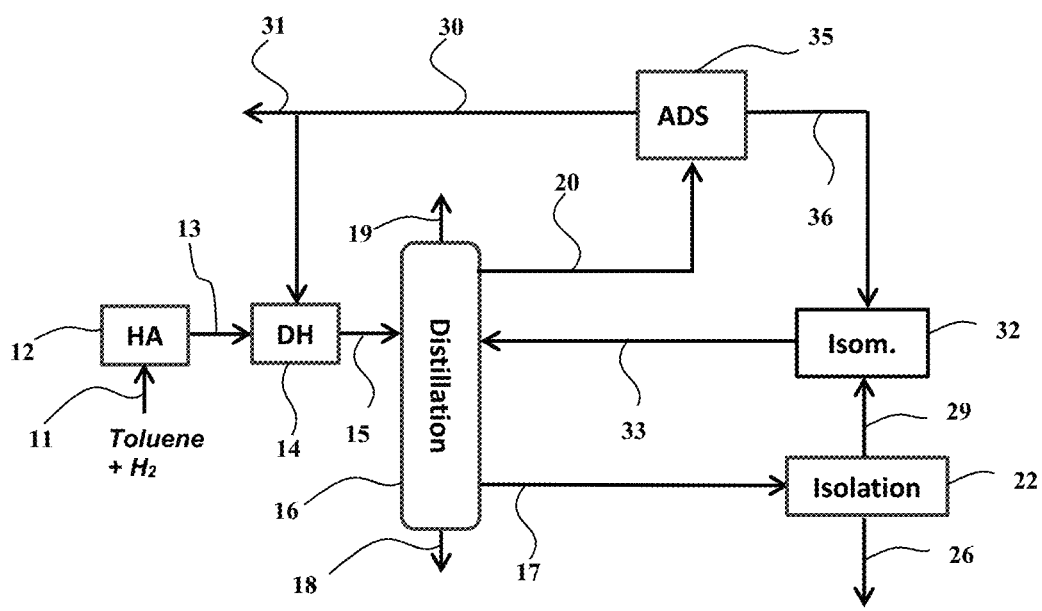
FIG. 4 is a flow diagram of a process for producing DMBP isomers from toluene according to one embodiment of the present disclosure.

Another embodiment of a process for producing DMBP isomers from a toluene-containing feed is illustrated in FIG. 4, in which toluene and hydrogen are fed by a single line 11 or, if preferred by separate lines (not shown), to a hydroalkylation unit 12. The hydroalkylation unit 12 contains a bed of a bifunctional catalyst which comprises a hydrogenation component and a solid acid alkylation component and which converts at least part of the toluene to (methylcyclohexyl) toluene (MCHT). The effluent from the hydroalkylation unit 12, comprising MCHT and unreacted toluene is then fed via line 13 to a dehydrogenation unit 14 where the MCHT is dehydrogenated to produce dimethylbiphenyl (DMBP) and hydrogen.

The effluent from the dehydrogenation unit 14 is then fed via line 15 to a distillation unit 16, where the 3,3', 3,4'- and 4,4'-DMBP isomers are separated and removed via line 17. More volatile unreacted MCHT and 2,X'-DMBP isomers are separated and removed via line 20. A heavy fraction is removed via line 18 and a light fraction via line 19.

Stream 20 is sent to a selective adsorption unit, which may comprise one or more adsorption steps and/or adsorbent types, which selectively adsorbs the 2,X'-DMBP isomers which are then recovered via extract stream 36. The extract stream 36 is then sent to isomerization unit 32, which affords a mixture of DMBP isomers. The effluent from the isomerization unit is fed via line 33 to the distillation unit. This process increases the overall amount of desirable 3,3'-, 3,4'- and 4,4'-DMBP isomers.

The other hydrocarbons in stream 20 are not adsorbed and exit the adsorption unit 35 as raffinate stream 30 which is supplied to the dehydrogenation unit. Residual MCHT in stream 30 is converted to DMBP in the dehydrogenation unit. Optionally, purge line 31 removes 1,X'-MCHT isomers and CPTs. In an alternate embodiment this stream may be at least partially recycled to the hydroalkylation unit to allow 1,X'-MCHTs to transalkylate to other MCHT isomers which may then be dehydrogenated to DMBP.

The raw DMBP-containing product leaving the distillation unit is fed via line 17 to an isolation unit 22 which isolates the 3,3'-, 3,4'- and 4,4'-DMBP isomers. The desired isomers leave the isolation unit as extract stream 26. Optionally, some of the isolated isomers may be sent to the isomerization unit 32, which affords flexibility to the process whereby the relative amounts of each of the DMBP isomers may be controlled based on market needs.

Figure 5:
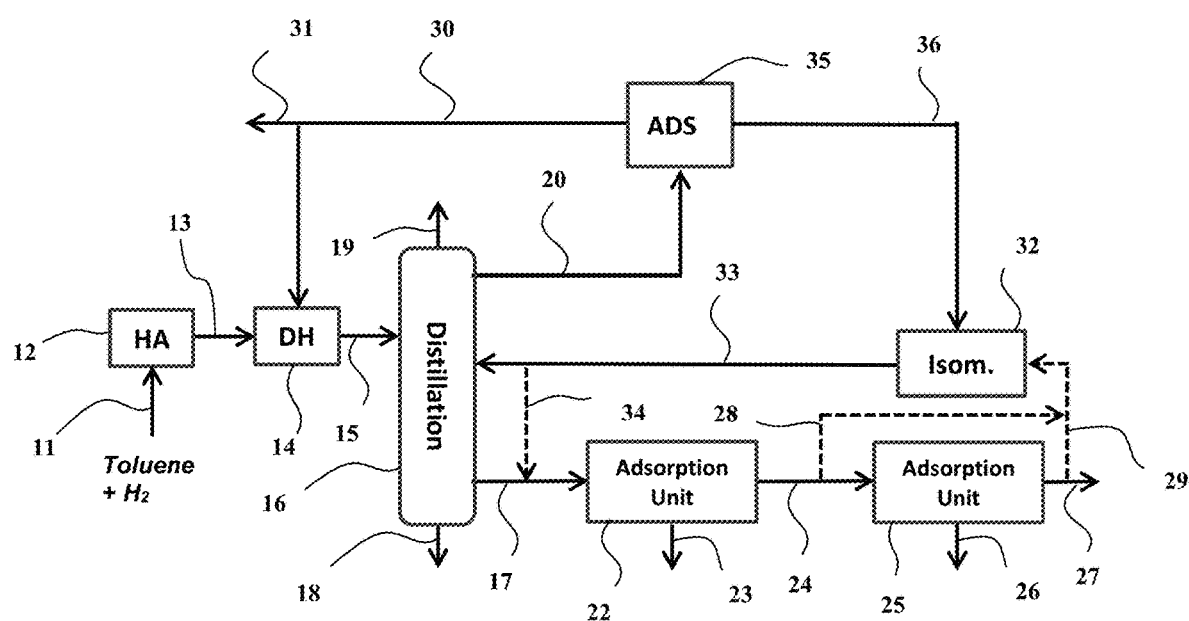
FIG. 5 is a flow diagram of a process for producing isomerically pure DMBP isomers from toluene according to one embodiment of the present disclosure.

Another embodiment of a process for producing DMBP isomers from a toluene-containing feed is illustrated in FIG. 5, in which toluene and hydrogen are fed by a single line 11 or, if preferred by separate lines (not shown), to a hydroalkylation unit 12. The hydroalkylation unit 12 contains a bed of a bifunctional catalyst which comprises a hydrogenation component and a solid acid alkylation component and which converts at least part of the toluene to (methylcyclohexyl) toluene (MCHT). The effluent from the hydroalkylation unit 12, comprising MCHT and unreacted toluene is then fed via line 13 to a dehydrogenation unit 14 where the MCHT is dehydrogenated to produce dimethylbiphenyl (DMBP) and hydrogen.

The effluent from the dehydrogenation unit 14 is then fed via line 15 to a distillation unit 16, where the 3,3'-, 3,4'- and 4,4'-DMBP isomers are separated and removed via line 17. More volatile unreacted MCHT and 2,X'-DMBP isomers are separated and removed via line 20. A heavy fraction is removed via line 18 and a light fraction via line 19.

Stream 20 is sent to a selective adsorption unit, which may comprise one or more adsorption steps and/or adsorbent types, which selectively adsorbs the 2,X'-DMBP isomers which are then recovered via extract stream 36. The extract stream 36 is then sent to isomerization unit 32, which affords a mixture of DMBP isomers. The effluent from the isomerization unit is fed via line 33 to the distillation unit. This process increases the overall amount of desirable 3,3'-, 3,4'- and 4,4'-DMBP isomers.

The other hydrocarbons in stream 20 are not adsorbed and exit the adsorption unit 35 as raffinate stream 30 which is supplied to the dehydrogenation unit. Residual MCHT in stream 30 is converted to DMBP in the dehydrogenation unit. Optionally, purge line 31 removes 1,X'-MCHT isomers and CPTs. In an alternate embodiment this stream may be at least partially recycled to the hydroalkylation unit to allow 1,X'-MCHTs to transalkylate to other MCHT isomers which may then be dehydrogenated to DMBP.

The raw DMBP-containing product leaving the distillation unit is then fed via line 17 to a first adsorption unit 22 which preferentially adsorbs 4,4'-DMBP which exits the adsorption unit as a stream rich in 4,4'-DMBP via line 23. The remaining 4,4'-DMBP depleted stream which contains 3,3'- and 3,4'-DMBP exits via line 24. The mixture of 3,3'- and 3,4'-DMBP is then fed via line 24 to a second adsorption unit 25 which separates the 3,4'-DMBP via line 26 from 3,3'-DMBP via line 27.

Optionally, some or all of stream 24 may be fed via line 28 to isomerization unit 32, which affords a mixture of DMBP isomers. Similarly, and optionally, some or all of stream 27 may be fed to the isomerization unit via line 29. The effluent from the isomerization unit is fed via line 33 to the distillation column. This affords flexibility to the process whereby the relative amounts of each of the DMBP isomers may be controlled based on market needs. Optionally, and depending on stream content, the output of the isomerization unit may be wholly or partly fed to the first adsorption unit via line 34.

Figure 6:
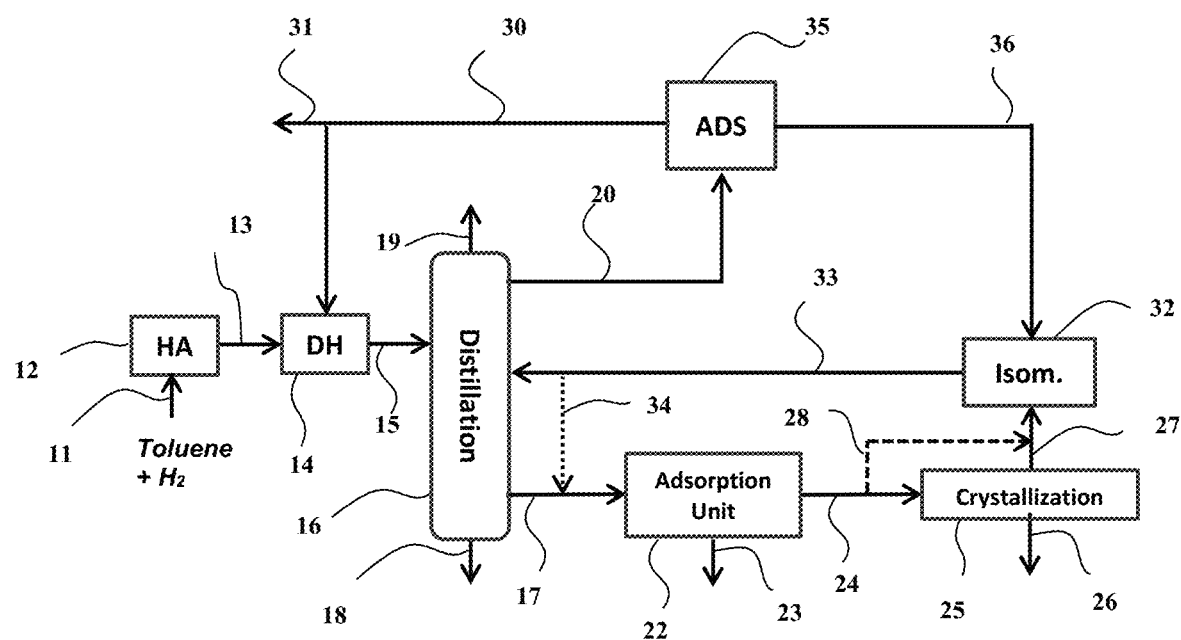
FIG. 6 is a flow diagram of a process for producing isomerically pure DMBP isomers from toluene according to one embodiment of the present disclosure.

Another embodiment of a process for producing DMBP isomers from a toluene-containing feed is illustrated in FIG. 6, in which toluene and hydrogen are fed by a single line 11 or, if preferred by separate lines (not shown), to a hydroalkylation unit 12. The hydroalkylation unit 12 contains a bed of a bifunctional catalyst which comprises a hydrogenation component and a solid acid alkylation component and which converts at least part of the toluene to (methylcyclohexyl) toluene (MCHT). The effluent from the hydroalkylation unit 12, comprising MCHT and unreacted toluene is then fed via line 13 to a dehydrogenation unit 14 where the MCHT is dehydrogenated to produce dimethylbiphenyl (DMBP) and hydrogen.

The effluent from the dehydrogenation unit 14 is then fed via line 15 to a distillation unit 16, where the 3,3'-, 3,4'- and 4,4'-DMBP isomers are separated and removed via line 17. More volatile unreacted MCHT and 2,X'-DMBP isomers are separated and removed via line 20. A heavy fraction is removed via line 18 and a light fraction via line 19.

Stream 20 is sent to a selective adsorption unit, which may comprise one or more adsorption steps and or absorbent types, which selectively adsorbs the 2,X'-DMBP isomers which are then recovered via extract stream 36. The extract stream 36 is then sent to isomerization unit 32, which affords a mixture of DMBP isomers. The effluent from the isomerization unit is fed via line 33 to the distillation unit. This process increases the overall amount of desirable 3,3'-, 3,4'- and 4,4'-DMBP isomers.

The other hydrocarbons in stream 20 are not adsorbed and exit the adsorption unit 35 as raffinate stream 30 which is supplied to the dehydrogenation unit. Residual MCHT in stream 30 is converted to DMBP in the dehydrogenation unit. Optionally, purge line 31 removes 1,X'-MCHT isomers and CPTs. In an alternate embodiment this stream may be at least partially recycled to the hydroalkylation unit to allow 1,X'-MCHTs to transalkylate to other MCHT isomers which may then be dehydrogenated to DMBP.

The raw DMBP-containing product leaving the distillation unit is then fed via line 17 to adsorption unit 22 which preferentially adsorbs 4,4'-DMBP which exits the adsorption unit as a stream rich in 4,4'-DMBP via line 23. The remaining 4,4'-DMBP depleted stream which contains 3,3'- and 3,4'-DMBP exits via line 24. The mixture of 3,3'- and 3,4'-DMBP is then fed via line 24 to a crystallization unit 25 which separates the 3,4'-DMBP via line 26 from 3,3'-DMBP via line 27.

Optionally, some or all of stream 24 may be fed via line 28 to isomerization unit 32, which affords a mixture of DMBP isomers. The effluent from the isomerization unit is fed via line 33 to the distillation unit. This affords flexibility to the process whereby the relative amounts of each of the DMBP isomers may be controlled based on market needs. Optionally, and depending on stream content, the output of the isomerization unit may be wholly or partly fed to the adsorption unit via line 34.

Figure 7:
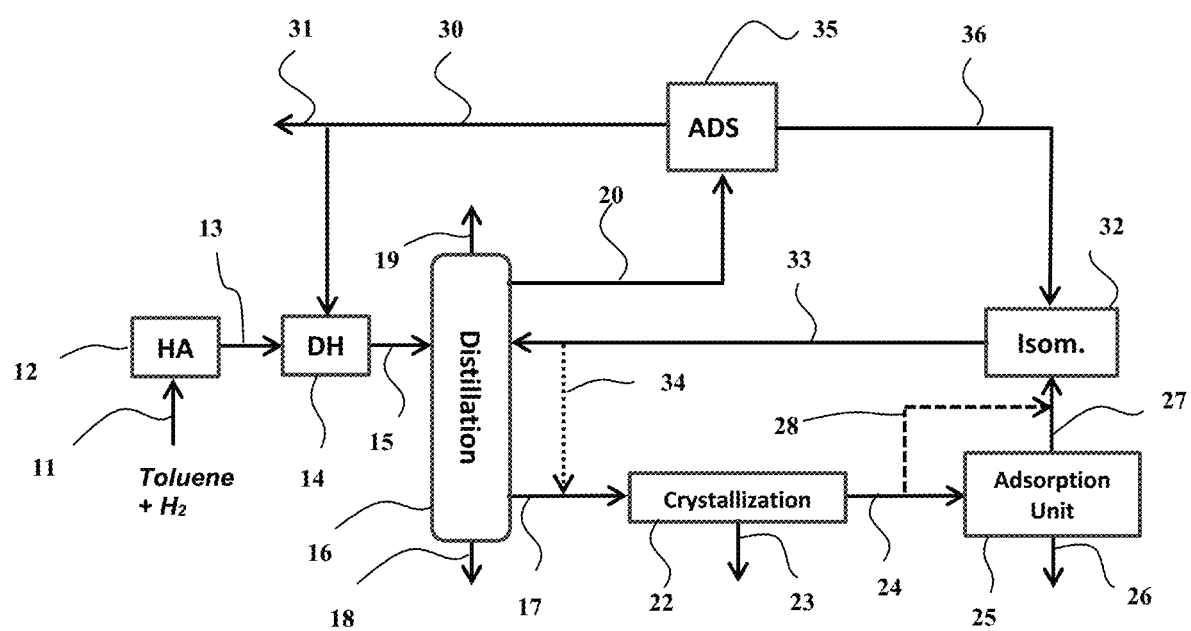
FIG. 7 is a flow diagram of a process for producing isomerically pure DMBP isomers from toluene according to one embodiment of the present disclosure.

Another embodiment of a process for producing DMBP isomers from a toluene-containing feed is illustrated in FIG. 7, in which toluene and hydrogen are fed by a single line 11 or, if preferred by separate lines (not shown), to a hydroalkylation unit 12. The hydroalkylation unit 12 contains a bed of a bifunctional catalyst which comprises a hydrogenation component and a solid acid alkylation component and which converts at least part of the toluene to (methylcyclohexyl) toluene (MCHT). The effluent from the hydroalkylation unit 12, comprising MCHT and unreacted toluene is then fed via line 13 to a dehydrogenation unit 14 where the MCHT is dehydrogenated to produce dimethylbiphenyl (DMBP) and hydrogen.

The effluent from the dehydrogenation unit 14 is then fed via line 15 to a distillation unit 16, where the 3,3'-, 3,4'- and 4,4'-DMBP isomers are separated and removed via line 17. More volatile unreacted MCHT and 2,X'-DMBP isomers are separated and removed via line 20. A heavy fraction is removed via line 18 and a light fraction via line 19.

Stream 20 is sent to a selective adsorption unit, which may comprise one or more adsorption steps and/or adsorbent types, which selectively adsorbs the 2,X'-DMBP isomers which are then recovered via extract stream 36. The extract stream 36 is then sent to isomerization unit 32, which affords a mixture of DMBP isomers. The effluent from the isomerization unit is fed via line 33 to the distillation unit. This process increases the overall amount of desirable 3,3'-, 3,4'- and 4,4'-DMBP isomers.

The other hydrocarbons in stream 20 are not adsorbed and exit the adsorption unit 35 as raffinate stream 30 which is supplied to the dehydrogenation unit. Residual MCHT in stream 30 is converted to DMBP in the dehydrogenation unit. Optionally, purge line 31 removes 1,X'-MCHT isomers and CPTs. In an alternate embodiment this stream may be at least partially recycled to the hydroalkylation unit to allow 1,X'-MCHTs to transalkylate to other MCHT isomers which may then be dehydrogenated to DMBP.

The raw DMBP-containing product leaving the distillation unit is then fed via line 17 to crystallization unit 22 which preferentially crystallizes 4,4'-DMBP which exits the adsorption unit as a stream rich in 4,4'-DMBP via line 23. The stream with reduced concentration of 4,4'-DMBP and contains 3,3'- and 3,4'-DMBP exits via line 24. The mixture of 3,3'- and 3,4'-DMBP is then fed via line 24 to adsorption unit 25 which separates the 3,4'-DMBP via line 26 from the mixture of 3,3'- and the remaining 4,4'-DMBP via line 27.

Optionally, some or all of stream 24 may be fed via line 28 to isomerization unit 32, which affords a mixture of DMBP isomers. The effluent from the isomerization unit is fed via line 33 to the distillation column. This affords flexibility to the process whereby the relative amounts of each of the DMBP isomers may be controlled based on market needs. Optionally, and depending on stream content, the output of the isomerization unit may be wholly or partly fed to the crystallization unit via line 34.

Selective Adsorbents

In some embodiments the adsorbent of the present disclosure is a zeolite or zeolite analogue.

In some embodiments the adsorbent is at least one zeolite, wherein said zeolite has a largest diffuse along dimension of at least about 4 Angstroms (Å).

In other embodiments the adsorbent is at least one zeolite, wherein said zeolite comprises one or more metal cations in the +1 or +2 oxidation states.

In other embodiments the adsorbent is at least one zeolite, wherein said zeolite has a largest diffuse along dimension of at least about 4 Angstroms (Å) and wherein said zeolite comprises one or more metal cations in the +1 or +2 oxidation states.

Preferably the largest diffuse along dimension of the zeolite is at least about 4.5 Å, or at least about 5.0 Å, or at least about 5.5 Å, or at least about 6.0 Å, or at least about 6.5 Å, or at least about 7.0 Å.

Preferably the largest diffuse along dimension of the zeolite is between about 4.0 Å and about 8.0 Å, or between about 4.5 Å and about 8.0 Å, or between about 5.0 Å and about 8.0 Å, or between about 5.5 Å and about 8.0 Å, or between about 6.0 Å and about 8.0 Å, or between about 6.5 Å and about 8.0 Å.

Numerous zeolite structural types are useful as selective adsorbents in the present processes, for example, BEA, FAU, MFI, MEL, MTW, MOR, LTL, EMT, FER, MAZ, MEI, TON, MWW, EUO, MFS, IMF, MRE, ITN, MTT, MSE and IWV.

Preferred zeolites comprise a 12-ring zeolite, an 11-ring zeolite or a 10-ring zeolite.

In some embodiments the zeolite comprises one or more alkali metal cations, alkaline earth metal cations, transition metal cations, rare earth metal cations or combinations thereof. Preferred cations are alkali metal or alkaline earth cations.

The zeolite may comprise one or more metal cations, wherein the ionic radius of the metal cation is between about 0.8 Å and about 2.0 Å.

The molar ratio of metal cations relative to aluminum in the zeolite may be between about 0.01 and about 2.0, or between about 0.05 and about 1.5, or between about 0.1 and about 1.0.

It has been discovered that particular metal cations improve the separation of particular DMBP isomers. The separation may be based on preferential adsorption of one or more DMBP isomers within the pores of the zeolite.

It has also been discovered that the crystallite size of the zeolite may improve the adsorptive ability.

The average crystallite size of the zeolite may be less than about 1000 nm, or less than about 500 nm, or less than about 200 nm, or less than about 100 nm, or less than about 100 nm.

The average crystallite size of the zeolite may be from about 1 to about 1000 nm, or from about 5 to about 500 nm, or from about 10 to about 100 nm.

In some embodiments, the zeolite is substantially metal cation free.

Both the natural and synthetic zeolites may be used as adsorbents in the processes of the present disclosure. A zeolite encompassed by the present disclosure for use as an adsorbent includes aluminosilicate cage structures in which the alumina and silica tetrahedra are intimately connected with each other in an open three-dimensional crystalline network. The tetrahedra are cross-linked by the sharing of oxygen atoms. The spaces between the tetrahedra are occupied by water molecules prior to dehydration. Subsequent partial or total dehydration results in crystals interlaced with channels of molecular dimensions. In the hydrated form, the crystalline aluminosilicates may be represented by the formula

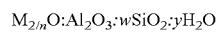

$$M_{2/n}O:Al_2O_3:wSiO_2:yH_2O$$

where M is a metal cation which balances the electrovalence of the tetrahedra, n represents the valence of the metal cation, w represents the mols of SiO and Y, the mols of water. The metal cations may be any one of a number of cations such as for example the alkali metal cations or the alkaline earth cations or other selected metal cations.

Zeolites which find use as adsorbents in the process of the present disclosure may possess relatively well-defined pore structure. The exact zeolite type is generally referred to by the particular silica-alumina ratio and the pore dimensions of the cage structures. For example, the faujasites are commonly represented as type X and type Y aluminosilicates and are defined by their varying silica to alumina ratios.

Cationic exchange or base exchange methods are generally known to those familiar with the field of zeolite production and are generally performed by contacting a zeolite with an aqueous solution of soluble salts of the cation or cations desired to be exchanged on the zeolite. The desired degree of cation exchange is allowed to take place before the zeolite is removed from the aqueous solution and dried to a desired water content. It is contemplated that in cationic exchange or base exchange methods that the cation exchange may take place using individual solutions of desired cations to be placed on the zeolite or can use exchange solutions containing mixtures of the cations which are desired to be exchanged onto the zeolite.

Preferably the metal cations are selected from the group consisting of potassium, rubidium, cesium, barium, copper, silver, lithium, sodium, beryllium, magnesium, calcium, strontium, cadmium, cobalt, nickel, manganese and zinc and combinations thereof.

In one preferred embodiment of the adsorptive separation processes herein disclosed when the separation of 2,X'-DMBP isomers (where X=1, 2 or 3) from non-DMBP components is desired improved results can be attained by choosing a potassium cation. This system displays a pronounced selectivity for the adsorption of 2,X'-DMBP isomers (where X=1, 2 or 3) as compared to non-DMBP components.

In another preferred embodiment of the adsorptive separation processes herein disclosed when the separation of 3,3'-DMBP from its isomeric mixtures is desired improved results can be attained by choosing a potassium or barium cation or mixtures thereof and performing the separation in iso-octane solvent. This system displays a pronounced selectivity for the adsorption of 3,3'-DMBP as compared to 3,4'-DMBP and 4,4'-DMBP.

In another preferred embodiment of the adsorptive separation processes herein disclosed when the separation of 3,4'-DMBP from its isomeric mixtures is desired improved results can be attained by choosing a cesium cation and performing the separation in mesitylene. This system displays a pronounced selectivity for the adsorption of both 3,3'-DMBP and 4,4'-DMBP compared to 3,4'-DMBP.

In another preferred embodiment of the adsorptive separation processes herein disclosed when the preferred adsorption of 4,4'-DMBP from its isomeric mixtures is desired improved results can be attained by choosing a potassium cation and performing the separation in iso-octane. This system displays a pronounced selectivity for the adsorption of 4,4'-DMBP as compared to 3,3'-DMBP and 3,4'-DMBP.

In separating the 3,3'-DMBP isomer in the process of this disclosure a bed of solid adsorbent may be contacted with a feed mixture, the 3,3'-DMBP is preferentially adsorbed on the adsorbent, the unabsorbed or raffinate mixture is removed from the adsorbent bed, and the adsorbed 3,3'-DMBP is removed from the solid adsorbent.

In separating the 4,4'-DMBP isomer in the process of this disclosure a bed of solid adsorbent may be contacted with a feed mixture, the 4,4'-DMBP is preferentially adsorbed on the adsorbent, the unabsorbed or raffinate mixture is removed from the adsorbent bed, and the adsorbed 4,4'-DMBP is removed from the solid adsorbent.

In separating the 3,4'-DMBP isomer in the process of this disclosure a bed of solid adsorbent may be contacted with a feed mixture, the 3,3'-DMBP and 4,4'-DMBP are preferentially adsorbed on the adsorbent, the unabsorbed 3,4'-DMBP is removed from the adsorbent bed, and the adsorbed 3,3'-DMBP and 4,4'-DMBP removed from the solid adsorbent.

The solvent used in the adsorptive separations of the processes of the present disclosure should be a material that is separable from the mixture that is fed to the solid adsorbent. In desorbing the adsorbed component of the feed, both the solvent and the desorbed feed component are removed from the adsorbent bed as a mixture, and without a method of separation of these two materials the purity of the adsorbed component of the feed would not be very high. Therefore, it is contemplated that a solvent that is of a different boiling range than the feed mixture fed to the solid adsorbent be used in this separation process. The use of a solvent of a differing boiling range would allow fractionation or other separation methods to be used to separate the selectively adsorbed feed component as a relatively pure product stream and allow recovery of the solvent for possible recycle in the process.

Solvents which can be used in the adsorptive separation processes of the present disclosure include, for example, iso-octane and mesitylene. Iso-octane and mesitylene have boiling points of 99 and 165° C. respectively, which are significantly lower than the boiling points of any one of the DMBP isomers and MCHT isomers (see Table 1).

The adsorbent can be contained in a single vessel where, through programmed flow into and out of the vessel, a separation of a desired DMBP isomer is effected. Swing bed operational techniques where a series of adsorbent vessels are available or simulated moving bed countercurrent operations may be used. In the latter method of operations the selection of a suitable solvent requires that it be capable of readily displacing a particular adsorbed DMBP isomer from the adsorbent.

Preparation of Metal Cation Treated Zeolite Adsorbents

The following general method was followed. About 100 g of NaY zeolite (Grace-Davison) was mixed with about 1000 g of a 0.4 M solution of the metal chloride in water. The mixture was left for 1 hr at ambient temperature, filtered and the filter cake washed with 3 L of water. The procedure was repeated using a 0.2 M metal chloride solution in water and the filter cake dried at 100° C. and then calcined in air for 2 hours at 300° C. The process was repeated twice more using 0.2 M metal chloride solution and the final filter cake dried at 110° C. Elemental compositions of some of the adsorbents prepared are shown in Table 4. USY 390 is a comparative example. The remaining zeolites are examples according to the present disclosure.

TABLE 4

| Elemental composition of zeolites used in adsorption experiments | | | | | | | |
|---|---|---|---|---|---|---|---|
| Mole ratio | USY 390 | NaY | MgY | KY | SrY | CsY | KBeta |
| Si/Al | 315 | 2.42 | 2.55 | 2.44 | 2.55 | 2.56 | 5.16 |
| Na/Al | 0.23 | 0.98 | 0.19 | 0.07 | 0.11 | 0.26 | 0 |
| Mg/Al | 0 | 0 | 0.39 | 0 | 0 | 0 | 0 |
| K/Al | 0 | 0 | 0 | 0.94 | 0 | 0 | 0.93 |
| Sr/Al | 0 | 0 | 0 | 0 | 0.47 | 0 | 0 |
| Cs/Al | 0 | 0 | 0 | 0 | 0 | 0.65 | 0 |

Preparation of Nano-Crystallite Zeolites

The method of Tokay B., Nanoparticle silicalite-1 crystallization from clear solutions: Nucleation, Microporous and Mesoporous Materials, Volume 118, Issues 1-3, 2009, Pages 143-151, was followed.

To a plastic beaker while stirring vigorously was added 146.64 g of distilled water to 57.96 g of tetrapropylammonium hydroxide (TPA-OH). Stirring was continued and 98.95 g of tetraethylorthosilicate (TEOS) was added to the mixture. This was allowed to stir covered (foil over top of beaker) for 4 hours. After 4 hours, the beaker was uncovered and the mixture allowed to stir for ~16 h. The mixture was then poured into 300 cc autoclave and heated to 90° C. at a rate of 0.5 C/min and held at a temperature of 90° C. for 70 h. The product was discharged from the autoclave and centrifuged. It was washed three times with water and centrifuged each time. The white crystalline product was dried in a drying oven at 100° C. overnight and then calcined in a calcination furnace by ramping to 600° C. at 5° C./min in air and holding at 600° C. overnight ~16 h. The product had a crystallite size of <100 nm as determined by scanning electron microscopy.

Batch Adsorption Experiments

Various adsorbents were evaluated for the separation of dimethyl biphenyl (DMBP) isomer mixtures utilizing batch experiments. The adsorbents were dried under vacuum (25 inch Hg) at 220° C. The dried solid materials were placed in a vial along with the DMBP mixture solution. The DMBP mixture solution was prepared by diluting a mixture of the isomers comprising about 25% by weight 3,3'-isomer, 55% by weight 3,4-isomer and 20% by weight 4,4'-isomer in a solvent such as isooctane or mesitylene. The total DMBP isomer content in the starting liquid phase was about 10% by weight. For the experiments with 2,X'-DMBP isomers a mixture of the 2,3'-DMBP and 2,4'-DMBP-isomers along with 3,2'-, 4,3'- and 4,4'-methylcyclohexyl toluene (MCHT) isomers was prepared. All the preparations were performed in an inert atmosphere dry box to minimize moisture exposure. The liquid/solid mixture was then agitated in a shaker at room temperature overnight (>16 hrs). The supernatant liquid phase was subsequently analyzed by gas chromatography (GC) to obtain the DMBP concentration. Solvents used were ACS grade or higher as available. DMBP isomer mixtures were either synthesized in house via methods described in, for example, WO 2015/112252, or prepared using purchased pure isomers.

Isolation of 2,X'-DMBP Isomers

Figure 8:
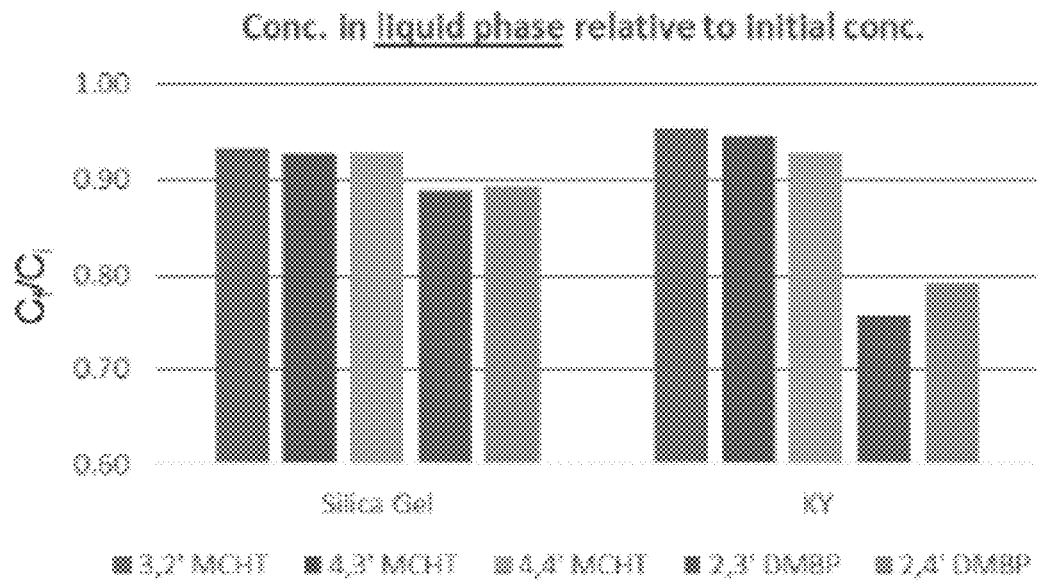
FIG. 8 is a bar chart illustrating the relative adsorptions of 3,2'-MCHT, 4,3'-MCHT, 4,4'-MCHT, 2,3'-DMBP and 2,4'-DMBP with silica gel and potassium treated Y zeolite.

FIG. 8 illustrates the results of batch adsorption experiments utilizing Y zeolite treated with potassium cations. For each test the amount of the hydrocarbon adsorbed is shown. The smaller the value of Cf/Ci, the more of a particular hydrocarbon is adsorbed. Ci is the initial concentration in the liquid phase and Cf is the final concentration in the liquid phase. The experiments demonstrate that 2,3'-DMBP and 2,4'-DMBP-isomers (the two right hand columns of the right hand set of results) are selectively adsorbed relative to MCHT isomers. In contrast, there was very little difference in adsorption levels between DMBP and MCHT when a silica gel was utilized.

Isolation of 3,4'-DMBP

Figure 9:
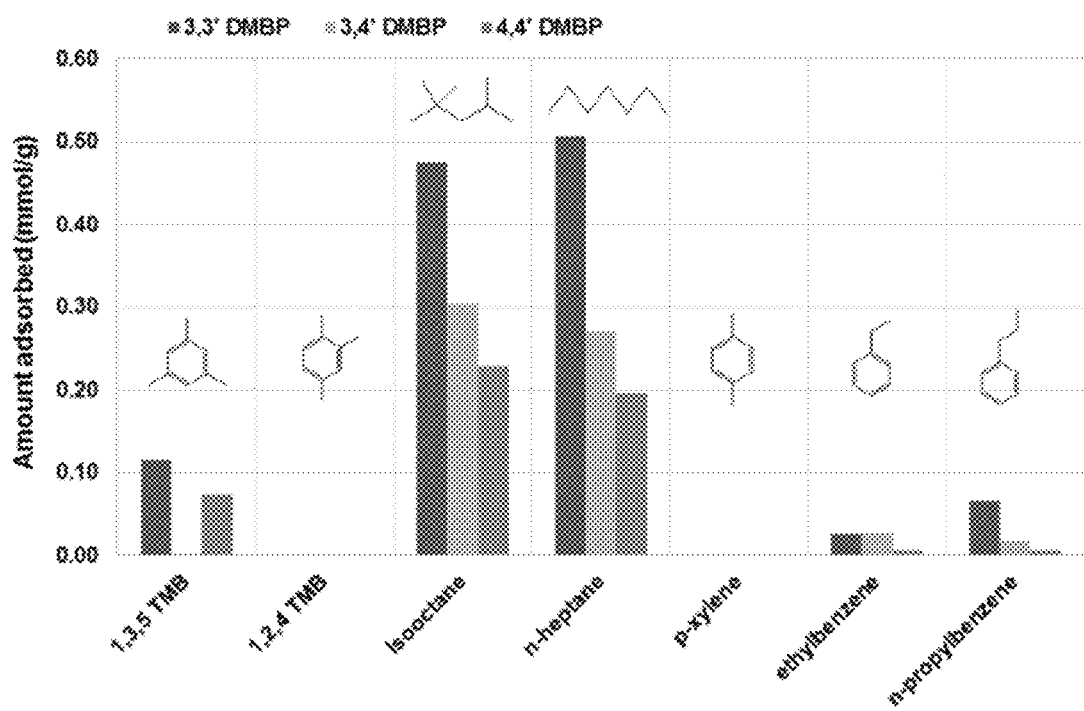
FIG. 9 is bar chart illustrating the effect of different solvents on the adsorption of 3,3'-DMBP, 3,4'-DMBP and 4,4'-DMBP on zeolite Y comprising potassium cations.

FIG. 9 illustrates the results of batch adsorption experiments with various solvents and utilizing Y zeolite treated with potassium cations. The solvents examined were 1,3,5-trimethylbenzene (1,3,5-TMB), 1,2,4-trimethylbenzene (1,2,4-TMB), iso-octane, n-heptane, p-xylene, ethylbenzene and n-propylbenzene. For each solvent the amount of each DMBP isomer adsorbed is indicated in mmol/g. The larger the bar the more of a particular isomer is adsorbed. For each solvent the bars represent 3,3'-DMBP, 3,4'-DMBP and 4,4'-DMBP from left to right respectively. It is apparent that the solvent choice causes different adsorption selectivity for different DMBP isomers. In the cases of 1,2,4-TMB and p-xylene no adsorption of any of the isomers was observed. Use of mesitylene (1,3,5-trimethylbenzene) shows selective adsorption of 3,3'- and 4,4'-DMBP. This selectivity allows isolation of 3,4'-DMBP from the mixture. Use of paraffinic solvents, like isooctane and n-heptane, results in a greater adsorption of 3,3'-DMBP.

Isolation of 4,4'-DMBP

Figure 10:
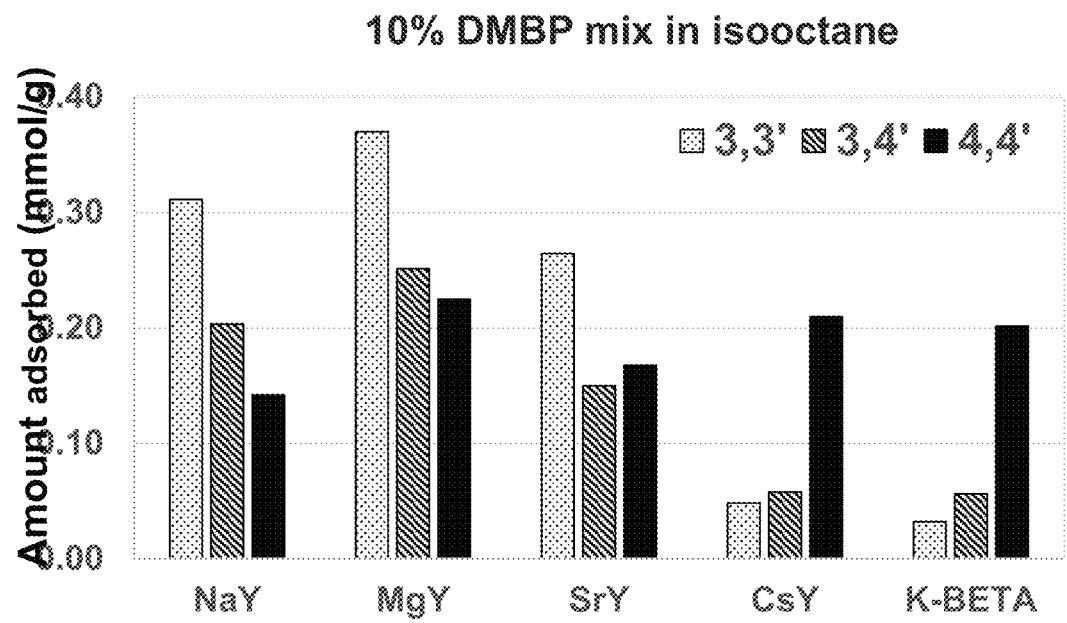
FIG. 10 is a bar chart illustrating the relative adsorptions of 3,3'-DMBP, 3,4'-DMBP and 4,4'-DMBP with various metal cation containing Y zeolites and potassium cation containing Beta zeolite using isooctane as a solvent.

FIG. 10 illustrates the results of batch adsorption experiments with isooctane as a solvent and magnesium, strontium and cesium treated Y zeolite. The cesium treated Y zeolite (CsY) adsorbs the 4,4' isomer more selectively than the other two isomers. This is surprising because other cation treated Y zeolites such as magnesium Y (MgY) and strontium Y (SrY) adsorb the 3,3' isomer more preferentially as found for KY. Adsorption of the 4,4'-isomer on CsY was three to four times higher than that of the other two isomers. Further, Beta zeolite treated with potassium cations indicated strong adsorption of the 4,4'-isomer.

Figure 11:
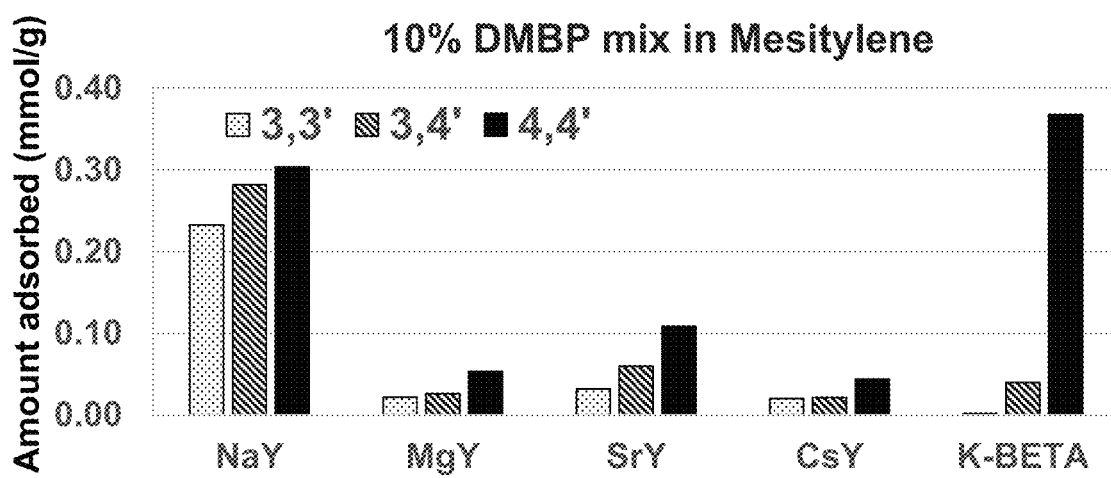
FIG. 11 is a bar chart illustrating the relative adsorptions of 3,3'-DMBP, 3,4'-DMBP and 4,4'-DMBP with various metal cation containing Y zeolites and potassium cation containing Beta zeolite using mesitylene as a solvent.

FIG. 11 illustrates the results of batch adsorption experiments with mesitylene as a solvent and magnesium, strontium and cesium treated Y zeolite and potassium treated Beta zeolite. Use of mesitylene causes selective adsorption of the 4,4'-isomer on all of these zeolites. Adsorption of the 4,4' isomer on the adsorbents was twice or more as compared to that of the other two isomers. All adsorptions of DMBP with mesitylene solvent were lower than those obtained with isooctane solvent, however K-Beta zeolite showed high and very selective adsorption of the 4,4'-isomer.

Isolation of 4,4'-DMBP

Figure 12:
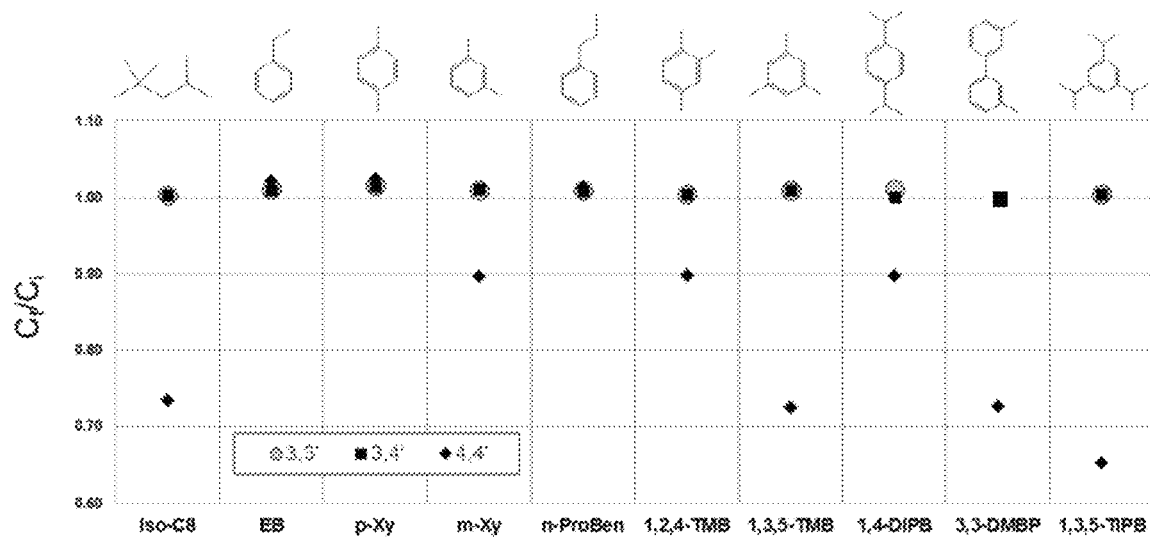
FIG. 12 is a plot of concentration changes (Cf/Ci) in the liquid phase after adsorption of DMBP isomers on ZSM-5 zeolite using various solvents at room temperature.

FIG. 12 illustrates the results of batch adsorption experiments with various solvents and utilizing ZSM-5 zeolite having a crystallite size between 2 and 5 μm and a Si/Al ratio of 220. The sodium content was <0.03 wt. %. The solvents examined were iso-octane, ethylbenzene, p-xylene, m-xylene, n-propylbenzene, 1,2,4-trimethylbenzene (1,2,4-TMB), 1,3,5-trimethylbenzene (1,3,5-TMB), 1,4-diisopropylbenzene, 3,3-DMBP and 1,3,5-triisopropylbenzene. For each solvent the amount of each DMBP isomer adsorbed is shown. The smaller the value of Cf/Ci, the more of a particular isomer is adsorbed. Ci is the initial concentration in the liquid phase and Cf is the final concentration in the liquid phase. It is apparent that ZSM-5 selectively adsorbs 4,4'-DMBP from a mixture of the isomers and that the solvent choice causes different adsorption selectivity for 4,4'-DMBP. Significantly, none of the solvents showed any adsorption of the other two isomers. This indicates 3,3'- and 3,4'-DMBP are excluded from the pores, allowing isolation of 4,4'-DMBP from the mixture. It also illustrates the strong effect of the solvents on how much of 4,4'-DMBP is adsorbed. Different solvents cause different degrees of adsorption. Bulkier solvent molecules, such as isooctane (2,2,4 trimethylpentane), mesitylene (1,3,5-trimethylbenzene), 1,4-diisopropylbenzene, and 1,3,5-triisopropylbenzene, result in more penetration of 4,4'-DMBP into the pores. Aromatic solvents with more branched alkyl chains (e.g. mesitylene and 1,2,4-trimethylbenzene) result in higher loading than those substituted with linear alkyl chains (e.g. n-propylbenzene).

Figure 13:
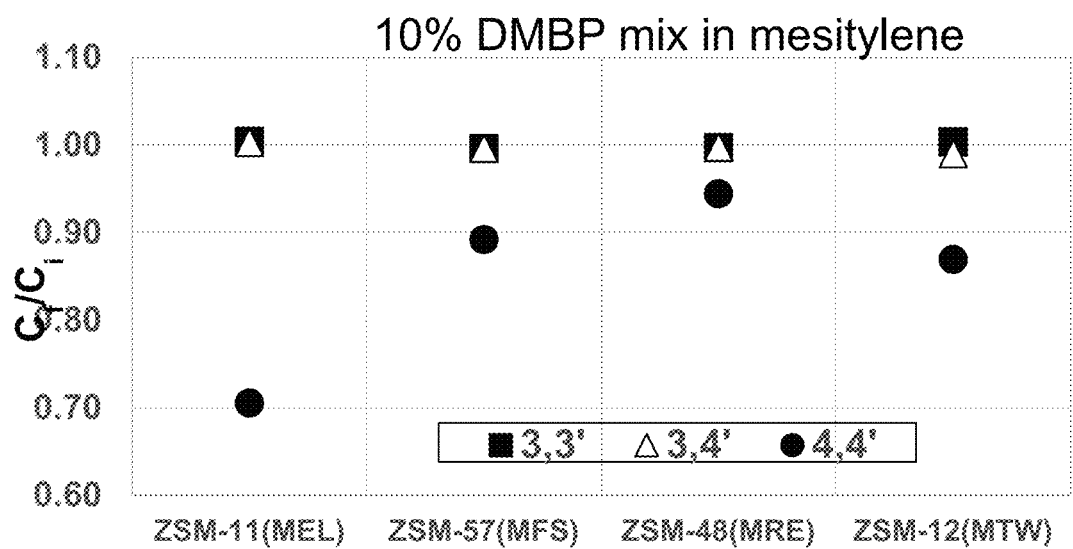
FIG. 13 is a plot of concentration changes (Cf/Ci) in the liquid phase after adsorption of DMBP isomers on various ZSM zeolite frameworks in mesitylene solvent at room temperature.

FIG. 13 is a plot of concentration changes (Cf/Ci) in the liquid phase after adsorption of DMBP isomers on various ZSM zeolite frameworks in mesitylene solvent at room temperature. In each case it can be seen that selective adsorption of the 4,4'-isomer occurred.

Influence of Crystallite Size

Figure 14:
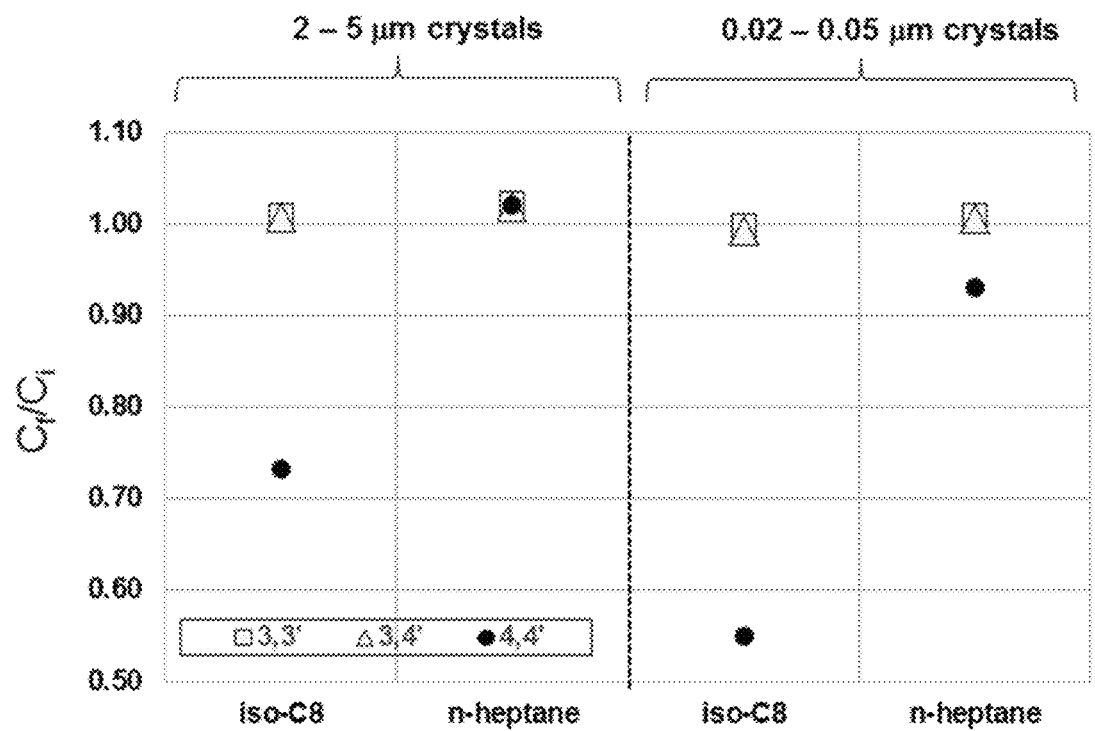
FIG. 14 is a plot of concentration changes (Cf/Ci) in the liquid phase after adsorption of DMBP isomers on two different sizes of ZSM-5 zeolite at room temperature.

FIG. 14 compares the effect of the size of the zeolite crystals on 4,4'-DMBP adsorption. The batch experimental data indicates that the small crystallite ZSM-5 (MFI) zeolite gives higher 4,4'-DMBP loading than the larger crystallite zeolite. For example, with n-heptane as the solvent, there was no selective adsorption of 4,4'-DMBP observed with the large crystal zeolite, whereas the small crystallite gave selective adsorption.

Continuous Breakthrough Experiments

A liquid chromatographic system was used for the breakthrough study of the adsorbents at elevated temperature. Adsorbents were packed into 4.6 mm ID×100 mm long stainless steel columns with 0.5 micron frits at each end. The adsorbents were dried at 300° C. for 1 hour in a flow of dry nitrogen. A packed column was equilibrated at 150° C. or 177° C. with a solvent (i.e. the mobile phase) prior to injection. The DMBP mixture solution (10 wt. % or 25 wt. %) was prepared in the same solvent as the mobile phase and introduced to a column through injection of a 6.6 ml pulse. The flow rate of solvent was set at 0.4 ml/min. Effluent from the column was collected in a fraction collector and the concentrations of DMBP in the fractions were determined by GC.

Isolation of 3,3'-DMBP

Figure 15:
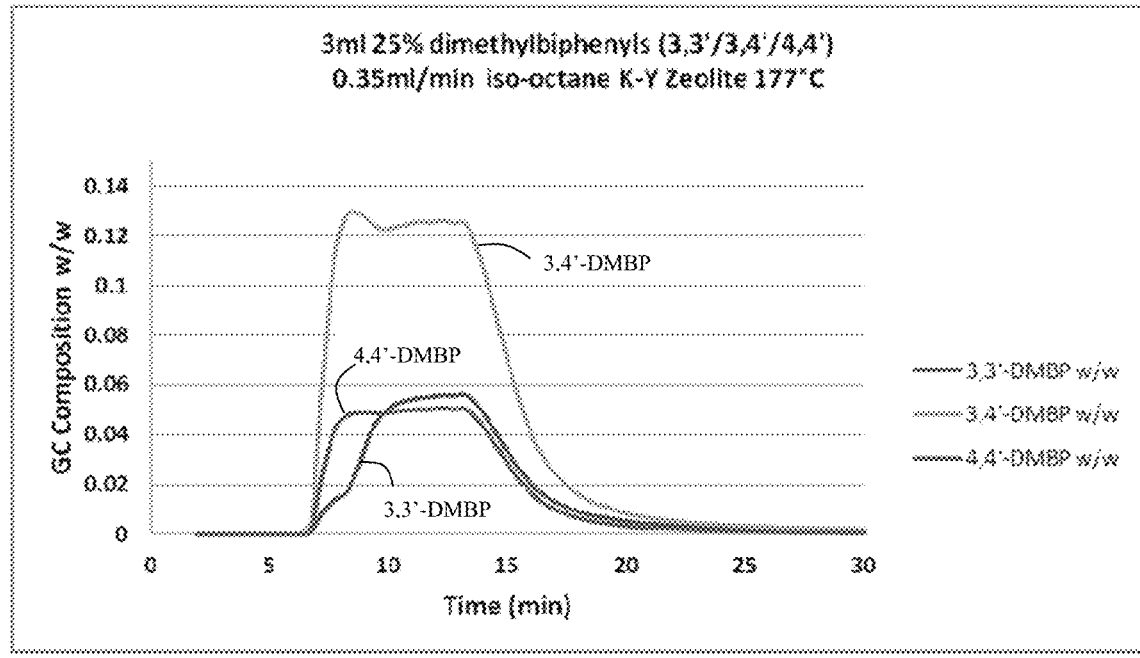
FIG. 15 illustrates the breakthrough curves for a mixture of 3,3'-DMBP, 3,4'-DMBP and 4,4'-DMBP in iso-octane solvent fed into a column containing Y zeolite containing potassium cations at 177° C.

A 3 ml pulse of 25 wt. % DMBP isomer mixture in iso-octane was introduced to a column containing potassium zeolite (Y-zeolite). FIG. 15 illustrates the breakthrough curves. The 3,3'-isomer was clearly retained as compared to the 4,4'-isomer and the 3,4'-isomer.

Figure 16:
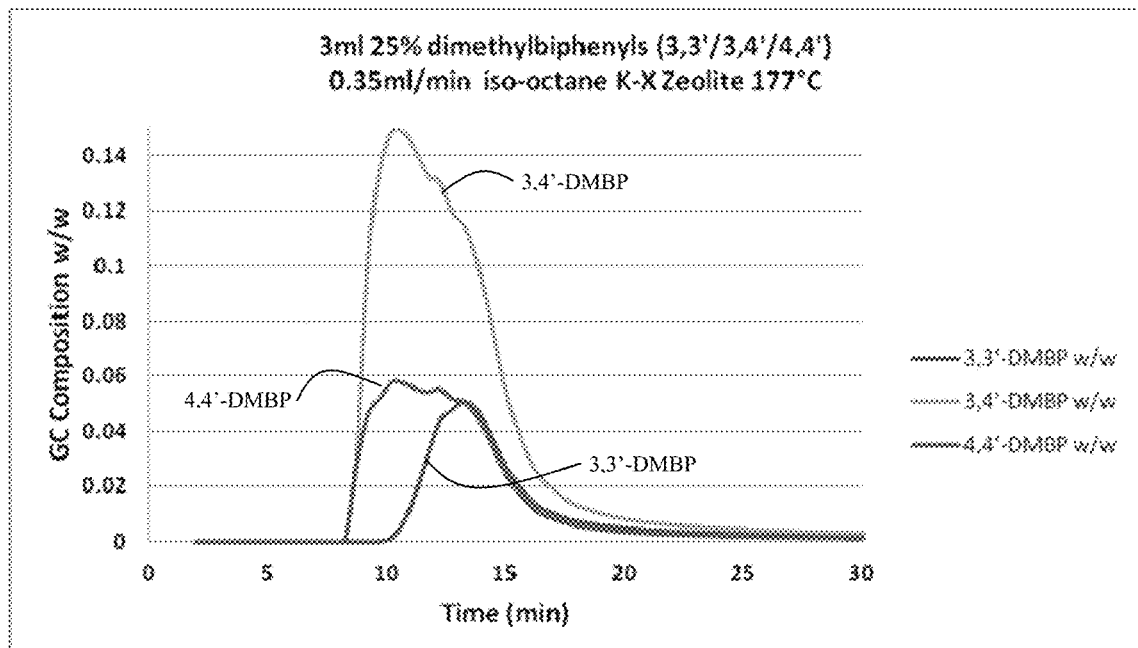
FIG. 16 illustrates the breakthrough curves for a mixture of 3,3'-DMBP, 3,4'-DMBP and 4,4'-DMBP in iso-octane solvent fed into a column containing X zeolite containing potassium cations at 177° C.

A 3 ml pulse of 25 wt. % DMBP isomer mixture in iso-octane was introduced to a column containing potassium zeolite (X-zeolite). FIG. 16 illustrates the breakthrough curves. The 3,3'-isomer was clearly retained as compared to the 4,4'-isomer and the 3,4'-isomer.

Figure 17:
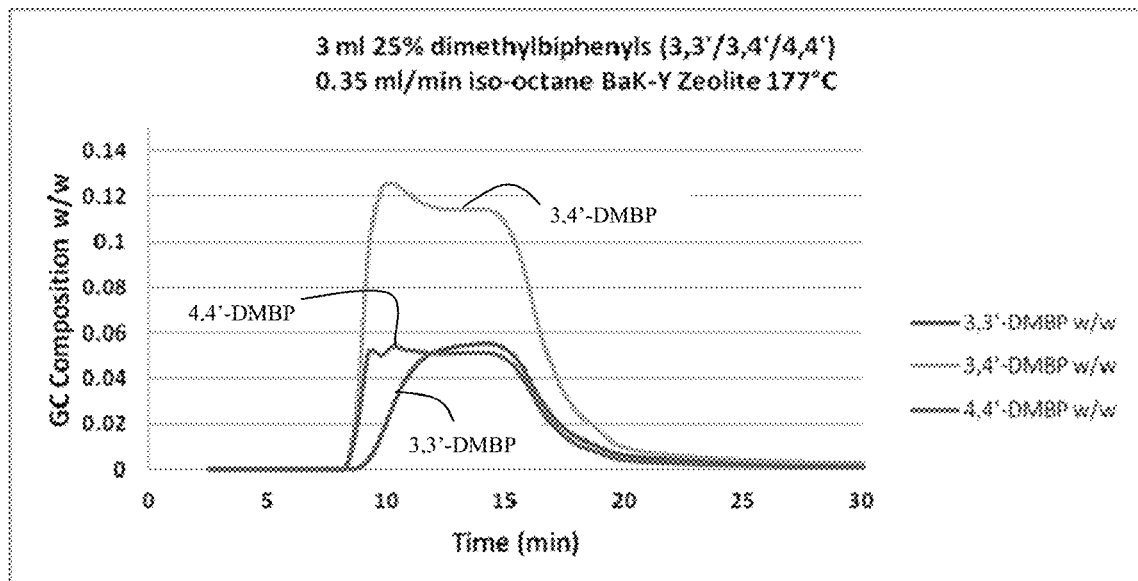
FIG. 17 illustrates the breakthrough curves for a mixture of 3,3'-DMBP, 3,4'-DMBP and 4,4'-DMBP in iso-octane solvent fed into a column containing Y zeolite containing potassium and barium cations at 177° C.

A 3 ml pulse of 25 wt. % DMBP isomer mixture in iso-octane was introduced to a column containing potassium barium zeolite (Y-zeolite). FIG. 17 illustrates the breakthrough curves. The 3,3'-isomer was clearly retained as compared to the 4,4'-isomer and the 3,4'-isomer.

Figure 18:
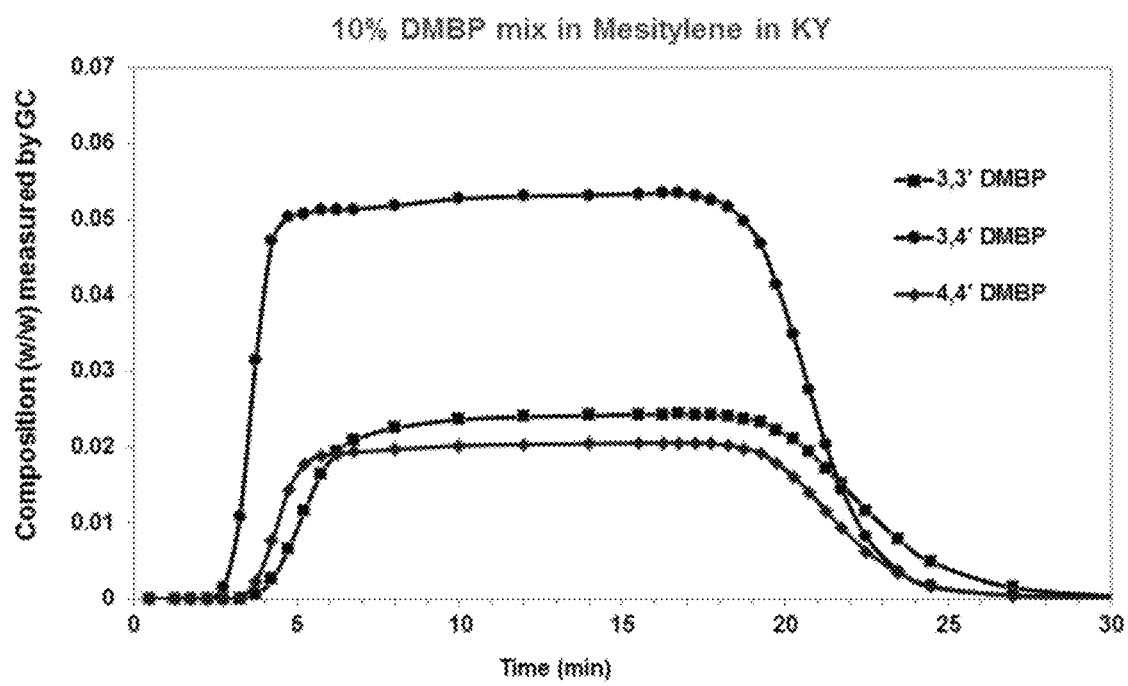
FIG. 18 illustrates the breakthrough curves for a mixture of 3,3'-DMBP, 3,4'-DMBP and 4,4'-DMBP in mesitylene solvent fed into a column containing Y zeolite containing potassium cations at 150° C.

Separation of the DMBP mixture on the KY with mesitylene was further tested in a liquid chromatographic system to validate the batch experiment data at the elevated temperature (150° C.). As shown in FIG. 18, the breakthrough point of the 3,4'-isomer is earlier than the other two isomers. This indicates no adsorption of the 3,4'-isomer, while the other two isomers show delayed breakthrough points due to their retention. The selective adsorption of the two isomers is consistent with what was observed from the batch experiment. The non-adsorbed isomer may be removed from the adsorbent and the adsorbed two isomers then recovered by desorption. The data also shows the 3,3' isomer is preferred to the 4,4'-isomer, thus presenting the possibility of separation of these two isomers into individual components.

Figure 19:
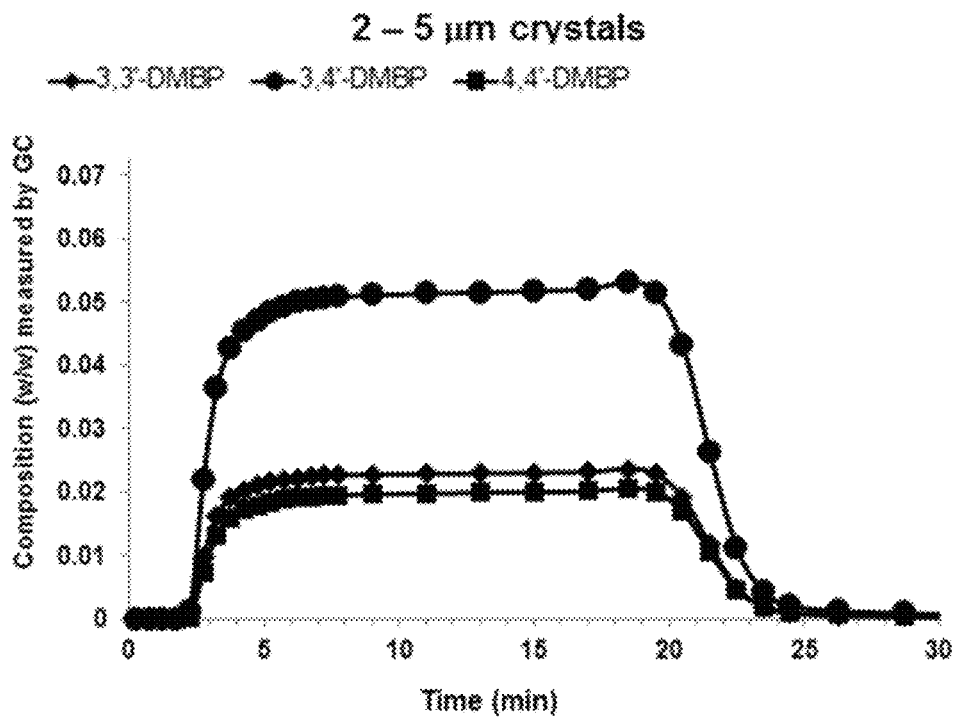
FIG. 19 illustrates the breakthrough curves for a mixture of 3,3'-DMBP, 3,4'-DMBP and 4,4'-DMBP in n-heptane solvent fed into a column containing ZSM-5 zeolite (2-5 μm crystallite size) at 150° C.
Figure 20:
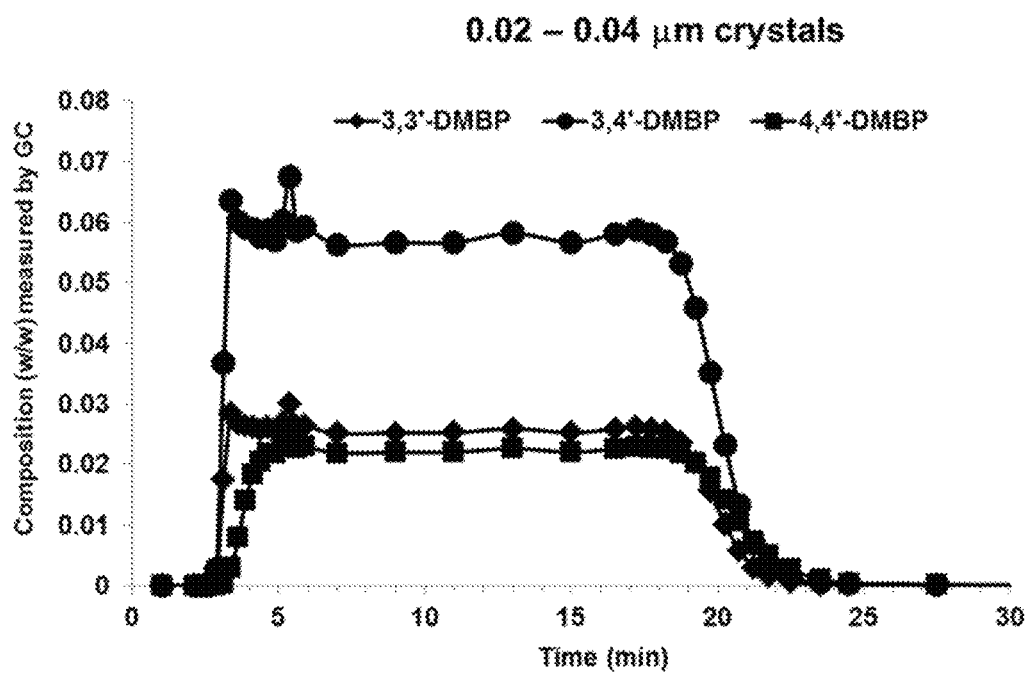
FIG. 20 illustrates the breakthrough curves for a mixture of 3,3'-DMBP, 3,4'-DMBP and 4,4'-DMBP in n-heptane solvent fed into a column containing ZSM-5 zeolite (0.02-0.04 μm crystallite size) at 150° C.

The effect of crystallite size was further tested by the breakthrough studies illustrated in FIGS. 19 and 20. A 3 ml pulse of 10 wt. % DMBP isomer mixture in n-heptane was introduced into columns containing large (2000 nm to 5000 nm) or small (<100 nm) crystallite ZSM-5 zeolite. The same trend that the small crystallite size increases adsorption of the 4,4'-isomer was observed. With n-heptane as the mobile phase, all three isomers eluted at the same time from the large crystallite zeolite column (FIG. 19), and their breakthrough times indicates no retention of these isomers. However, the small crystallite ZSM-5 (MFI) zeolite (FIG. 20) resulted in adsorption of 4,4'-DMBP under the same conditions, as evidenced by the delayed breakthrough point.

Figure 21:
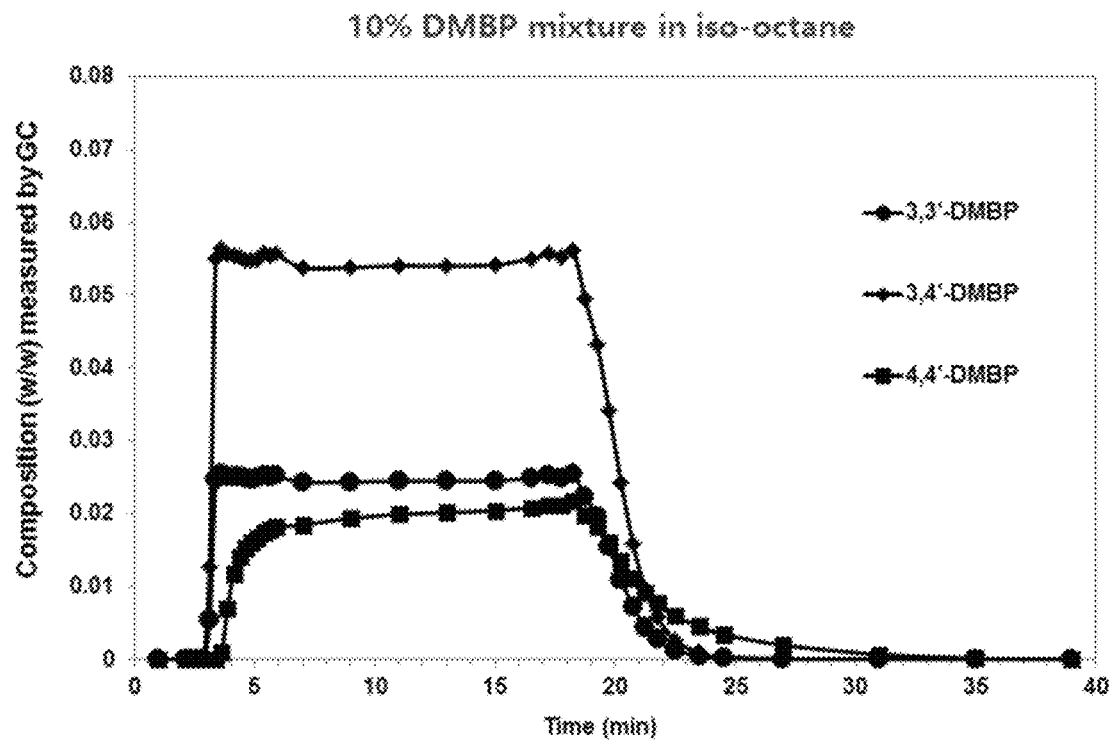
FIG. 21 illustrates the breakthrough curves for a mixture of 3,3'-DMBP, 3,4'-DMBP and 4,4'-DMBP in iso-octane solvent fed into a column containing ZSM-5 zeolite (0.02-0.04 μm crystallite size) at 150° C.
Figure 22:
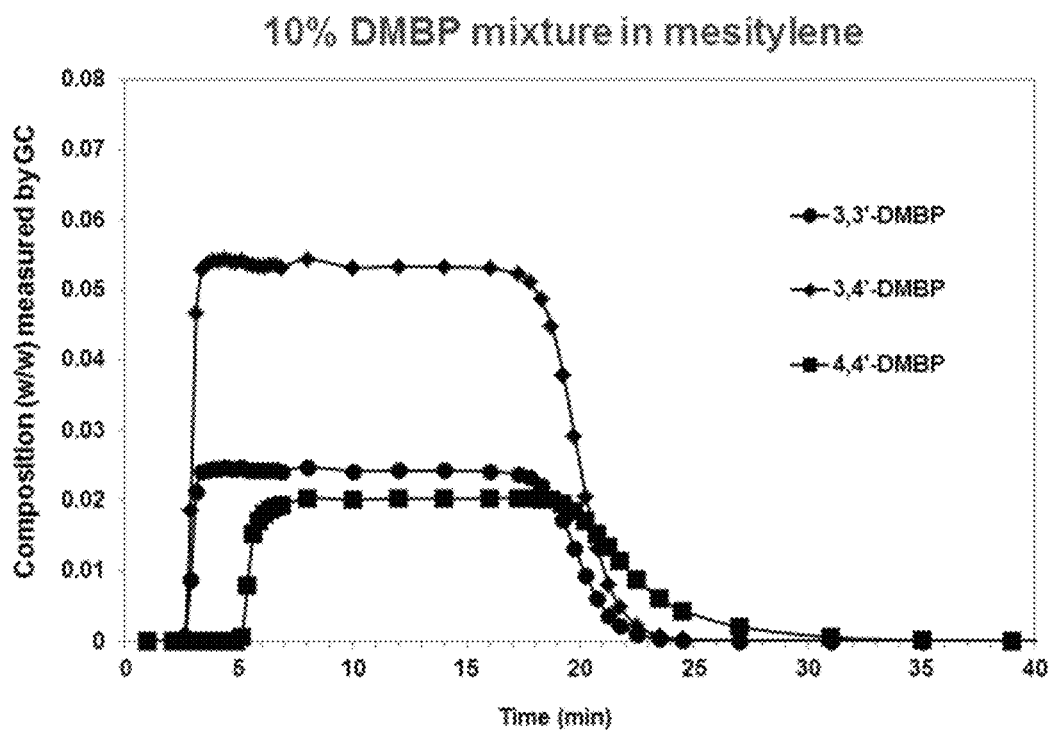
FIG. 22 illustrates the breakthrough curves for a mixture of 3,3'-DMBP, 3,4'-DMBP and 4,4'-DMBP in mesitylene solvent fed into a column containing ZSM-5 zeolite (0.02-0.04 μm crystallite size) at 150° C.

The effect of the solvent was also demonstrated by a breakthrough study at elevated temperature (150° C.). FIGS. 21 and 22 compare the breakthrough curves with different solvent systems and their impact on 4,4'-DMBP adsorption. Iso-octane and n-heptane are both paraffinic, but the branched bulkier iso-octane (FIG. 21) results in 4,4'-DMBP adsorption which is about two times higher than with n-heptane. The even bulkier mesitylene solvent (FIG. 22) increases the adsorption even more as compared to that with iso-octane. About three times more of 4,4'-DMBP adsorption was observed. Regardless of solvents tested, the 3,3' and 3,4'-DMBP isomers were not adsorbed. The ratio of the total peak area under the curves is consistent with the initial composition of the feed, indicating the complete recovery of the DMBP isomers from the column. In the process, the non-adsorbed 3,3'- and 3,4'-DMBP can be removed from adsorbents and the adsorbed 4,4'-DMBP is then recovered by desorption.

COMPARATIVE EXAMPLE

Figure 23:
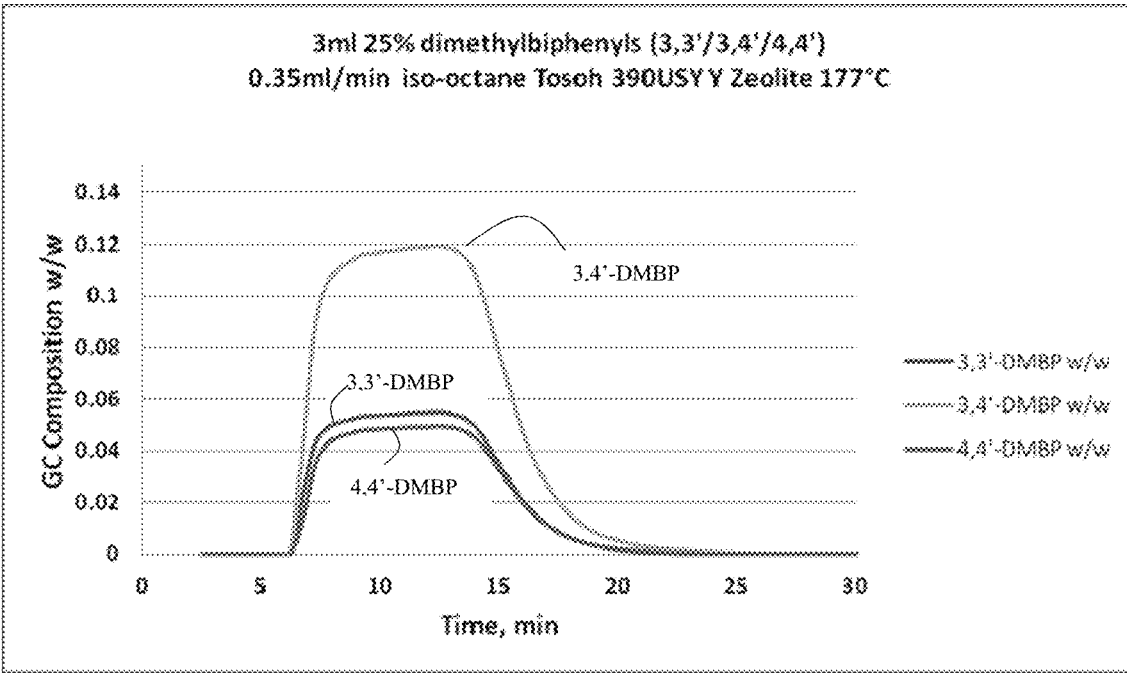
FIG. 23 illustrates the breakthrough curves for a mixture of 3,3'-DMBP, 3,4'-DMBP and 4,4'-DMBP in iso-octane solvent fed into a column containing high silica USY at 177° C.

For comparison, and to illustrate the effect of the metal cations in the zeolite, a high silica low metal cation faujasite (390 USY) was packed into a column and tested. This material has a high Si/Al ratio of 315 and a low Na/Al ratio of 0.23. FIG. 23 illustrates no selectivity for any of the isomers over the others.

It is to be understood that while the present disclosure has been described in conjunction with the specific embodiments thereof, the foregoing description is intended to illustrate and not limit the scope of the disclosure. Other aspects, advantages and modifications will be apparent to those skilled in the art to which the disclosure pertains. Therefore, the above examples are put forth to provide those skilled in the art with a complete disclosure and description of how to make and use the disclosed compositions, and are not intended to limit the scope of the disclosure.

For the sake of brevity, only certain ranges are explicitly disclosed herein. However, ranges from any lower limit may be combined with any upper limit to recite a range not explicitly recited, as well as, ranges from any lower limit may be combined with any other lower limit to recite a range not explicitly recited, in the same way, ranges from any upper limit may be combined with any other upper limit to recite a range not explicitly recited.

ADDITIONAL EMBODIMENTS

Embodiment 1

A process for separating one or more 2,X'-dimethyl biphenyl isomers (where X=2, 3 or 4) from a mixture comprising the same, the process comprising:
(a) contacting the mixture with a first adsorbent thereby selectively adsorbing one or more 2,X'-dimethyl biphenyl isomers (where X=2, 3 or 4) within said first adsorbent;
(b) withdrawing from said first adsorbent a first raffinate stream comprising one or more less selectively adsorbed components; and
(c) withdrawing from said first adsorbent a first extract stream comprising said one or more selectively adsorbed 2,X'-dimethyl biphenyl isomers (where X=2, 3 or 4).

Embodiment 2

A process for producing one or more 2,X'-dimethyl biphenyl isomers (where X=2, 3 or 4), the process comprising:
(a) contacting a feed comprising toluene with hydrogen in the presence of a hydroalkylation catalyst under conditions effective to produce a hydroalkylation reaction product comprising (methylcyclohexyl)toluenes;
(b) dehydrogenating at least part of the hydroalkylation reaction product in the presence of a dehydrogenation catalyst under conditions effective to produce a dehydrogenation reaction product comprising said dimethyl biphenyl isomers;
(c) separating the dehydrogenation reaction product into at least a first stream comprising one or more 3,3'-, 3,4'- and 4,4'-dimethyl biphenyl isomers and at least one second stream comprising one or more 2,X'-dimethyl biphenyl isomers (where X=2, 3 or 4);
(d) contacting the at least one second stream with a first adsorbent thereby selectively adsorbing one or more 2,X'-dimethyl biphenyl isomers (where X=2, 3 or 4) within said first adsorbent;
(e) withdrawing from said first adsorbent a first raffinate stream comprising one or more less selectively adsorbed components; and
(f) withdrawing from said first adsorbent a first extract stream comprising one or more selectively adsorbed 2,X'-dimethyl biphenyl isomers (where X=2, 3 or 4).

Embodiment 3

A process for producing one or more 3,3'-, 3,4'- and 4,4'-dimethyl biphenyl isomers, the process comprising:
(a) contacting a feed comprising toluene with hydrogen in the presence of a hydroalkylation catalyst under conditions effective to produce a hydroalkylation reaction product comprising (methylcyclohexyl)toluenes;
(b) dehydrogenating at least part of the hydroalkylation reaction product in the presence of a dehydrogenation catalyst under conditions effective to produce a dehydrogenation reaction product comprising said dimethyl biphenyl isomers;
(c) separating the dehydrogenation reaction product into at least a first stream comprising one or more 3,3'-, 3,4'- and 4,4'-dimethyl biphenyl isomers and at least one second stream comprising one or more 2,X'-dimethyl biphenyl isomers (where X=2, 3 or 4);
(d) contacting the at least one second stream with a first selective adsorbent thereby adsorbing one or more 2,X'-dimethyl biphenyl isomers (where X=2, 3 or 4) within said first adsorbent;
(e) withdrawing from said first adsorbent a first raffinate stream comprising one or more less selectively adsorbed components;
(f) withdrawing from said first adsorbent a first extract stream comprising one or more selectively adsorbed 2,X'-dimethyl biphenyl isomers (where X=2, 3 or 4);
(g) contacting said first extract stream with an isomerization catalyst under conditions effective to produce an isomerization effluent comprising one or more 3,3'-, 3,4'- or 4,4'-dimethyl biphenyl isomers.

Embodiment 4

A process according to embodiment 3, further comprising the step of feeding at least a portion of the isomerization effluent formed in step (g) to separation step (c).

Embodiment 5

A process according to any one of embodiments 2 to 4, wherein the separation of at least a first stream and at least one second stream comprises distillation and/or crystallization.

Embodiment 6

A process according to any one of embodiments 1 to 5, wherein the mixture of embodiment 1 or the second stream of embodiment 2 or embodiment 3 comprising 2,X'-dimethyl biphenyl isomers, where X=2, 3 or 4, further comprises one or more of cyclopentadienyl toluenes (CPDTs), 4-methylcyclohexyl toluenes (4,X'-MCHTs, where X=2, 3 or 4), 3-methylcyclohexyl toluenes (3,X'-MCHTs, where X=2, 3 or 4), 2-methylcyclohexyl toluenes (2,X'-MCHTs, where X=2, 3, or 4), ethylcyclopentyl toluenes (CPTs), 1-methylcyclohexyl toluenes (1,X'-MCHTs, where X=2, 3 or 4) and dimethyl bicyclohexanes (DMBCHs).

Embodiment 7

A process according to any one of embodiments 2 to 6, further comprising separating the 3,3'-3,4'- and 4,4'-dimethyl biphenyl isomers in the at least first stream, wherein said separation comprises at least one selective adsorption.

Embodiment 8

A process according to embodiment 7, wherein the separation of the 3,3'-, 3,4'- and 4,4'-dimethyl biphenyl isomers in the first stream comprises:
(i) contacting the first stream with a second adsorbent thereby selectively adsorbing at least one of the 3,3'-, 3,4'- or 4,4'-dimethyl biphenyl isomers within said second adsorbent;
(ii) withdrawing from said second adsorbent a second raffinate stream comprising less selectively adsorbed 3,3'-, 3,4'- or 4,4'-dimethyl biphenyl isomers; and
(iii) withdrawing from said second adsorbent a second extract stream comprising said selectively adsorbed 3,3'-, 3,4'- or 4,4'-dimethyl biphenyl isomers.

Embodiment 9

A process according to embodiment 8, further comprising:
(i) contacting the second raffinate stream with a third adsorbent thereby selectively adsorbing one of the 3,3'-, 3,4'- or 4,4'-dimethyl biphenyl isomers less selectively adsorbed by the second adsorbent; and
(ii) withdrawing from said third adsorbent a third extract stream comprising a less selectively adsorbed 3,3'-, 3,4'- or 4,4'-dimethyl biphenyl isomer and a fourth extract stream comprising said selectively adsorbed 3,3'-, 3,4'- or 4,4'-dimethyl biphenyl isomer.

Embodiment 10

A process according to embodiment 8, further comprising selectively crystallizing one of the 3,3'-, 3,4'- or 4,4'-dimethyl biphenyl isomers from the second raffinate stream.

Embodiment 11

A process according to any one of embodiments 3 to 6, wherein the separation of the 3,3'-, 3,4'- and 4,4'-dimethyl biphenyl isomers in the first stream comprises:
(i) crystallizing one of the 3,3'-, 3,4'- and 4,4'isomers to produce a product comprising that isomer and a third raffinate stream comprising non-crystallizing 3,3'-, 3,4'- or 4,4'-isomers;
(ii) contacting the third raffinate stream with a fourth adsorbent thereby selectively adsorbing at least one of the non-crystallizing 3,3'-, 3,4'- or 4,4'-isomers within said fourth adsorbent;
(iii) withdrawing from said fourth adsorbent a fourth raffinate stream comprising the less selectively adsorbed 3,3'-, 3,4'- or 4,4'-dimethyl biphenyl isomers; and
(iv) withdrawing from said fourth adsorbent a fifth extract stream comprising said selectively adsorbed 3,3'-, 3,4'- or 4,4'-dimethyl biphenyl isomers.

Embodiment 12

A process according to any one of embodiments 8 to 11, further comprising contacting at least part of any one or more of the second, third or fourth raffinate streams with an isomerization catalyst under conditions effective to produce an isomerization effluent comprising one or more 3,3'-, 3,4'- and 4,4'-dimethyl biphenyl isomers, wherein the relative ratios of the 3,3'-, 3,4'- and 4,4'-dimethyl biphenyl isomers after isomerization are different to the relative ratios prior to isomerization.

Embodiment 13

A process according to any one of embodiments 8 to 12 further comprising contacting at least part of one or more of the first to fifth extract streams with an isomerization catalyst under conditions effective to produce an isomerization effluent comprising one or more 3,3'-, 3,4'- and 4,4'-dimethyl biphenyl isomers, wherein the relative ratios of the 3,3'-, 3,4'- and 4,4'-dimethyl biphenyl isomers after isomerization are different to the relative ratios prior to isomerization.

Embodiment 14

A process according to any one of embodiments 12 or 13, wherein at least part of the isomerization effluent is fed to the separation step of either of embodiments 2 to 3 which affords at least a first stream and at least one second stream.

Embodiment 15

A process according to embodiment 3 or any one of embodiments 12 to 14, wherein at least part of the isomerization effluent is fed to the first adsorbent and/or subjected to crystallization to separate at least one of the 3,3'-, 3,4'- and 4,4'-dimethyl biphenyl isomers.

Embodiment 16

A process according to any one of embodiments 1 to 15, wherein one or more of the selective adsorptions are performed in the presence of one or more additional solvents.

Embodiment 17

A process according to embodiment 16, wherein the additional solvent comprises an aromatic hydrocarbon, a saturated hydrocarbon or combinations thereof.

Embodiment 18

A process according to any one of embodiments 2 to 17, wherein the feed which is separated into at least a first stream comprising one or more 3,3'-, 3,4'- and 4,4'-dimethyl biphenyl isomers and at least one second stream comprising one or more 2,X'-dimethyl biphenyl isomers (where X=2, 3 or 4), comprises 5-50% by weight 3,3'-isomer, 15-80% by weight 3,4'-isomer and 5-50% by weight 4,4'-isomer based on the total weight of the three isomers.

Embodiment 19

A process according to any one of embodiments 3 to 18, wherein the isomerization effluent comprises 10-60% by weight 3,3'-isomer, 10-60% by weight 3,4'-isomer, 2-30% by weight 4,4'-isomer and 2-30% by weight 2,X'-isomers (where X=2, 3 or 4) based on the total weight of the isomers.

Embodiment 20

A process according to any one of embodiments 1 to 19, wherein any one or more of the selective adsorptions comprise a simulated moving bed, membrane separation, or semi-batch (swing) adsorption.

Embodiment 21

A process according to any one of embodiments 1 to 20, wherein selective adsorption comprises contacting the mixture of dimethyl biphenyl isomers with at least one zeolite, wherein said zeolite has a largest diffuse along dimension of at least about 4 Angstroms (Å).

Embodiment 22

A process according to any one of embodiments 1 to 21, wherein selective adsorption comprises contacting the mixture of dimethyl biphenyl isomers with at least one zeolite, wherein said zeolite comprises one or more metal cations in the +1 or +2 oxidation states.

Embodiment 23

A process according to any one of embodiments 1 to 22, wherein selective adsorption comprises contacting the mixture of dimethyl biphenyl isomers with at least one zeolite, wherein said zeolite comprises an average crystallite size less than 1000 nm, or less than 100 nm.

Embodiment 24

A process according to any one of embodiments 1 to 23, wherein any one or more of the first to fourth adsorbents comprises a single adsorbent type, the adsorbent selectively adsorbing one or more dimethyl biphenyl isomers.

Embodiment 25

A process according to any one of embodiments 1 to 24, wherein any one or more of the first to fourth adsorbents comprises a mixture of more than one adsorbent types, the mixture selectively adsorbing one or more dimethyl biphenyl isomers.

Embodiment 26

A process according to any one of embodiments 1 to 25, wherein any one or more of the selective adsorptions is performed in one or more vessels, each containing one adsorbent type or multiple adsorbent types.

All documents cited herein are fully incorporated by reference for all jurisdictions in which such incorporation is permitted and to the extent such disclosure is consistent with the description of the present disclosure.

The invention claimed is:

1. A process for separating one or more 2,X'-dimethyl biphenyl isomers (where X=2, 3 or 4) from a mixture comprising the same the process comprising:
   (g) contacting the mixture with a first adsorbent comprising a zeolite having a structure of BEA, FAU, MFI, MEL, MTW, MOR, LTL, EMT, FER, MAZ, MEI, TON, MWW, EUO, MFS, IMF, MRE, ITN, MSE, MTT or IWV thereby selectively adsorbing one or more 2,X'-dimethyl biphenyl isomers (where X=2, 3 or 4) within said first adsorbent;
   (h) withdrawing from said first adsorbent a first raffinate stream comprising one or more less selectively adsorbed components; and
   (i) withdrawing from said first adsorbent a first extract stream comprising said one or more selectively adsorbed 2,X'-dimethyl biphenyl isomers (where X=2, 3 or 4);
wherein the mixture comprising 2,X'-dimethyl biphenyl isomers, where X=2, 3 or 4, further comprises one or more of cyclopentadienyl toluenes (CPDTs), 4-methylcyclohexyl toluenes (4,X'-MCHTs, where X=2, 3 or 4), 3-methyl cyclohexyl toluenes (3,X'-MCHTs, where X=2, 3 or 4), 2-methyl cyclohexyl toluenes (2,X'-MCHTs, where X=2, 3, or 4), ethylcyclopentyl toluenes (CPTs), 1-methylcyclohexyl toluenes (1,X'-MCHTs, where X=2, 3 or 4) and dimethyl bicyclohexanes (DMBCHs).

2. A process according to claim 1, wherein one or more of the selective adsorptions are performed in the presence of one or more additional solvents.

3. A process according to claim 2, wherein the additional solvent comprises an aromatic hydrocarbon, a saturated hydrocarbon or combinations thereof.

4. A process according to claim 1, wherein any one or more of the selective adsorptions comprise a simulated moving bed, membrane separation, or semi-batch (swing) adsorption.

5. A process according to claim 1, wherein selective adsorption comprises contacting the mixture of dimethyl biphenyl isomers with at least one zeolite, wherein said zeolite has a largest diffuse along dimension of at least about 4 Angstroms (Å).

6. A process according to claim 1, wherein selective adsorption comprises contacting the mixture of dimethyl biphenyl isomers with at least one zeolite, wherein said zeolite comprises one or more metal cations in the +1 or +2 oxidation states.

7. A process according to claim 1, wherein selective adsorption comprises contacting the mixture of dimethyl biphenyl isomers with at least one zeolite, wherein said zeolite comprises an average crystallite size less than 1000 nm, or less than 100 nm.

8. A process according to claim 1, wherein any one or more of the first to fourth adsorbents comprises a single adsorbent, the adsorbent selectively adsorbing one or more dimethyl biphenyl isomers.

9. A process according to claim 1, wherein any one or more of the first to fourth adsorbents comprises a mixture of more than one adsorbent types, the mixture selectively adsorbing one or more dimethyl biphenyl isomers.

10. A process according to claim 1, wherein any one or more of the selective adsorptions is performed in one or more vessels, each containing one adsorbent or multiple adsorbent.

* * * * *